US007470782B2

(12) United States Patent
Bruck et al.

(10) Patent No.: US 7,470,782 B2
(45) Date of Patent: Dec. 30, 2008

(54) CASB618 POLYNUCLEOTIDES AND POLYPEPTIDES AND THEIR USE

(75) Inventors: Claudine Elvire Marie Bruck, Rixensart (BE); Jean-Pol Cassart, Rixensart (BE); Thierry Coche, Rixensart (BE); Carlota Vinals Y De Bassols, Rixensart (BE)

(73) Assignee: GlaxoSmithKline Biologicals, S.A., Rixensart (BG)

( * ) Notice: Subject to any disclaimer, the term of this patent is extended or adjusted under 35 U.S.C. 154(b) by 240 days.

(21) Appl. No.: 11/199,820

(22) Filed: Aug. 9, 2005

(65) Prior Publication Data
US 2006/0052593 A1 Mar. 9, 2006

Related U.S. Application Data

(63) Continuation of application No. 09/936,456, filed as application No. PCT/EP00/02048 on Mar. 9, 2000, now abandoned.

(30) Foreign Application Priority Data

Mar. 11, 1999 (GB) .................................. 9905607.9
Sep. 1, 1999 (GB) .................................. 9920590.8

(51) Int. Cl.
C07H 21/04 (2006.01)
(52) U.S. Cl. .................................................... 536/23.1
(58) Field of Classification Search .................. None
See application file for complete search history.

(56) References Cited

U.S. PATENT DOCUMENTS 5,840,839 A 11/1998 Wang et al.
7,105,315 B2 9/2006 Lasek et al.

FOREIGN PATENT DOCUMENTS

| WO | WO95/17210  | 6/1995  |
| WO | WO96/08514  | 3/1996  |
| WO | WO98/32865  | 7/1998  |
| WO | WO99/49030  | 9/1999  |
| WO | WO99/49055  | 9/1999  |
| WO | WO/0061596  | 10/2000 |
| WO | WO/0056891  | 9/2001  |

OTHER PUBLICATIONS

EST Accession No. AI304327/c downloaded from http://es/ScoreAccessWeb/GetItem.action?AppId=11199820&seqId3 on Nov. 7, 2007.*
Boon, Advances in Cancer Research 58:177-210 (1992).
NCBI Accession No. 1BKN B (Jul. 9, 1998).
Ezzell, J. NIH Res. 7:46-49 (1995).
Gimmi, E. R., et al., Deletions in the SV40 late polyadenylation region downstream of the AATAAA mediate similar effects on expression in various mammalian cell lines, *Nucleic Acids* (1988)16(18): 8977-8997.

Ugozzoli, et al. "Combinations of protein polysaccharide conjugate vaccine for intranasal immunization." J. Infect. Dis. 186; 1358-1361 (2002).
Bravo, et al. "The new DTPw-HBV-Hib combination vaccine can be used at the WHO schedule with a monovalent dose of hepatitis B vaccine at birth." Southeast Asian J. Trop. Med. Public Health 29; 772-778 (1998).
Zepp, et al. "Evidence for induction of polysaccharide specific B-cell memory in the first year of life: plain Haemophilus influenzae type b-PRP (Hib) boosters children primed with a tetanus-conjugate HIb-DTPa-HBV combined vaccine." J. Pediatr 156; 18-24 (1997).
Richmond, et al. "Safety and immunogenicity of a new Neisseria meningitides serogroup C-tetanus toxoid conjugate vaccine in healthy adults." Vaccine 18; 641-646 (2000).
Choo, et al. "Immunogenicity and reactogenicity of a group C meningococcal conjugate vaccine compared with group A + C meningococcal polysaccharide vaccine in adolescents in a randomized observer-blind controlled trial." Vaccine 18; 2686-2692 (2000).
MacLennan, et al. "Safety, Immunogenicity and induction of immunologic memory by a serogroup C meningiciccal conjugate vaccine in infants." JAMA 283: 2795-2801 (2000).
Definition of "Celsius" in Merriam-Webster dictionary downloaded from url www. M-w.com on Jun. 26, 2004.
Ezzell, J NIH Res., (190): 1793-1799 (1995).
Van den Eynde et al., J. Exp. Med. (190):1793-1799 (1999).
Benjamini and Leskowitz, Immunology, A Short Course, Wiley-Liss, (1991) Chapter 3, pp. 37-45 only.
Fernandez, et al. "Randomised trial of the immunogenicity of fractional dose regiments of PRP-T *Haemophilus influenzae* type B conjugate Vaccine." Am. J. Trop. Med. Hyg. 62; 485-490 (2000).
A.H.F.S. Category 80:12 Haemophilus b. conjugate vaccine (Tetanus toxoid conjugate).
Spitler, *Cancer Biotherapy*, 1995, 10: 1-3.
Mankovich et al., *Journal of Bacteriology* (1989)171:5325-31.
Alberts et al., *Molecular Biology of the Cell*, 3rd Ed. (1994) 465.
Shantz and Pegg, *Int J of Biochem and Cell Biol*. (1999) (31): 107-122.
McClean and Hill, Eur J of Cancer (1993 (29A): 2243-2248.
Fu et al., EMBO Journal (196) (15) 4392-4401.
Riott et al., Immunoology, 4th Ed. 1996, Mosby pp. 7.8-7.12, and Chapter 10 only.
EMBL Sequence Database, Nov. 23, 1998, Accession No. A1274929.
EMBL Sequence Database, Nov. 24, 1998, Accession No. A1281211.
International Search Report from International Application No. PCT/EP00/02048.

* cited by examiner

*Primary Examiner*—Misook Yu
(74) *Attorney, Agent, or Firm*—Eric I. Kron

(57) ABSTRACT

CASB618 polypeptides and polynucleotides and methods for producing such polypeptides by recombinant techniques are disclosed. Also disclosed are methods for utilizing CASB618 polypeptides and polynucleotides in diagnostics, and vaccines for prophylactic and therapeutic treatment of cancers, particularly ovarian and colon cancers, autoimmune diseases, and related conditions.

2 Claims, 7 Drawing Sheets

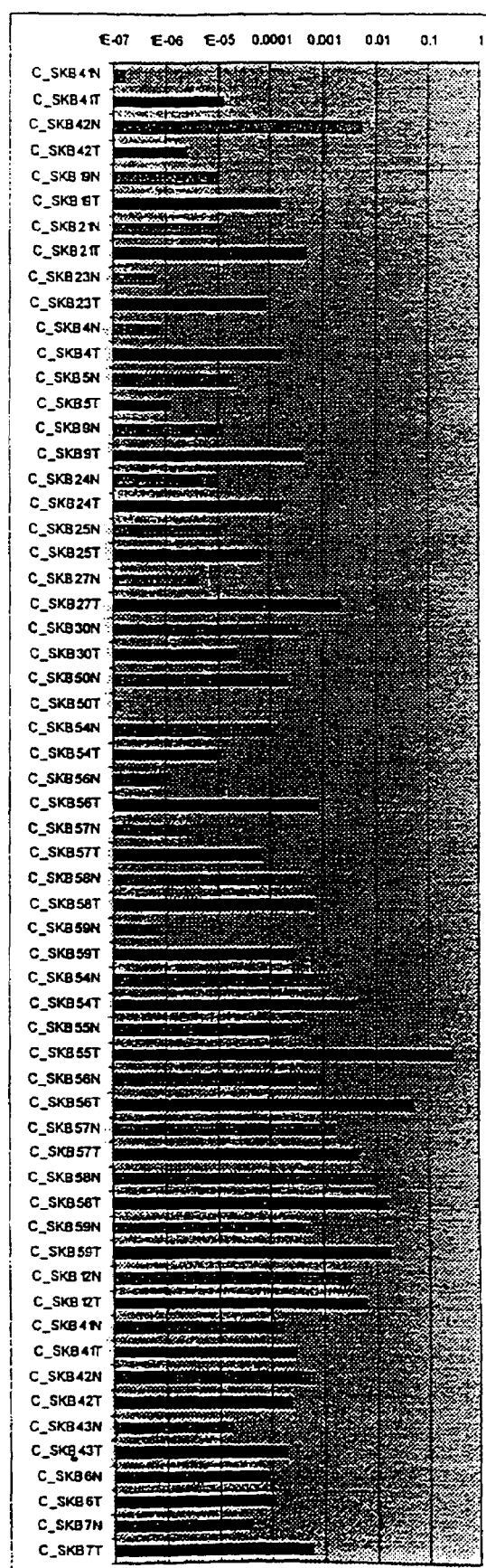
Figure 1: Expression levels of CASB618 in matched colon normal and tumoral samples.

Figure 2A: Expression of CASB618 in normal tissues: Real-time PCR results
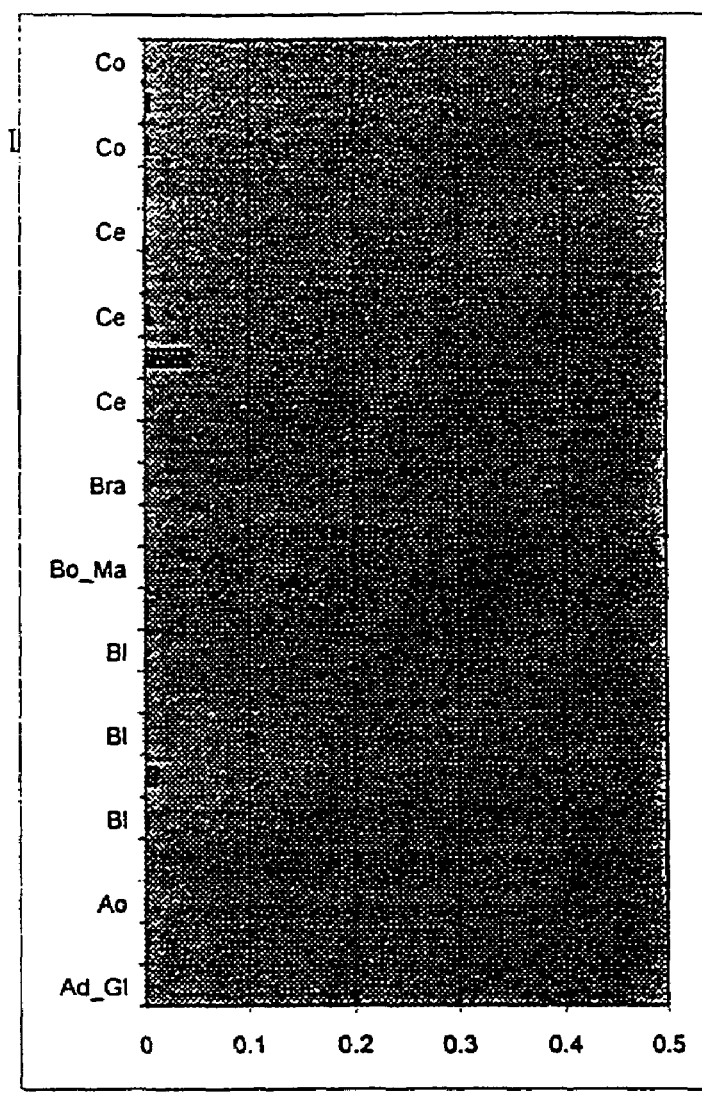

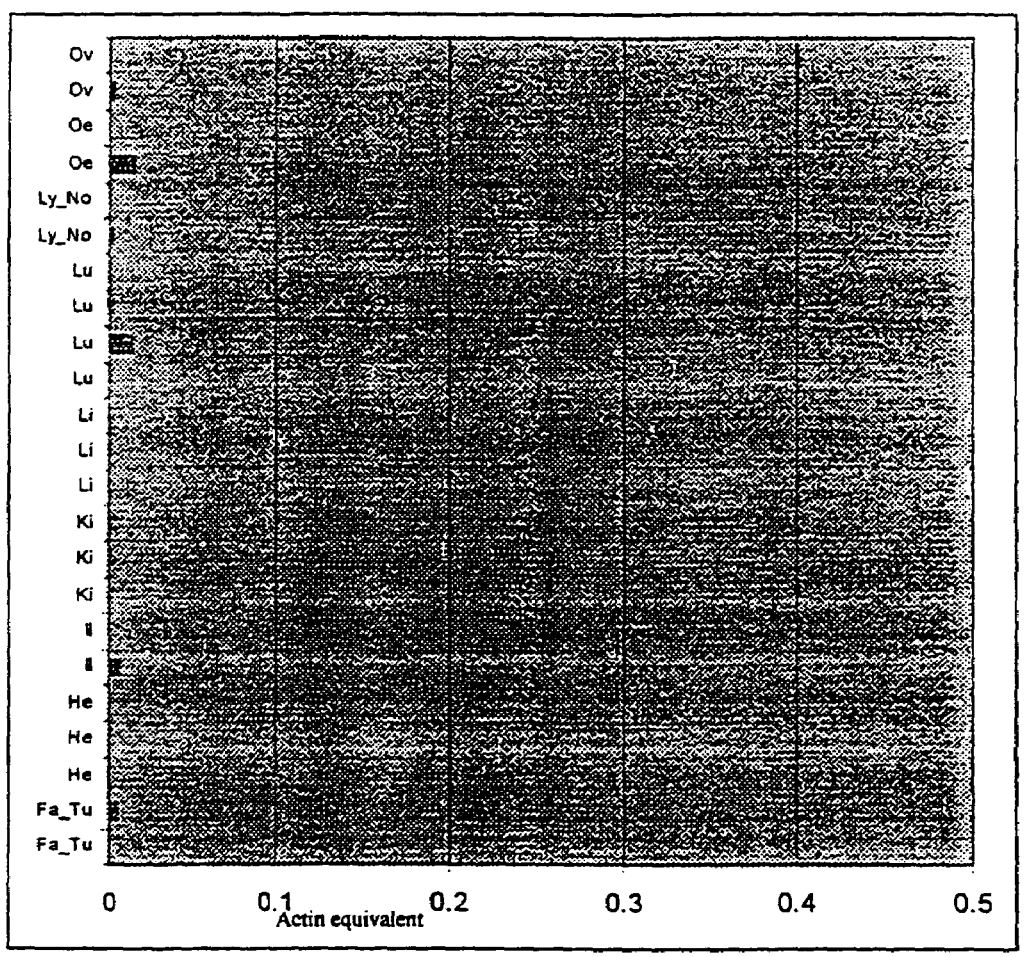
Figure 2B: Real-time PCR data of CASB618 expression in normal tissues (continued)

Figure 2C: Real-time PCR data of CASB618 expression in normal tissues (continued)
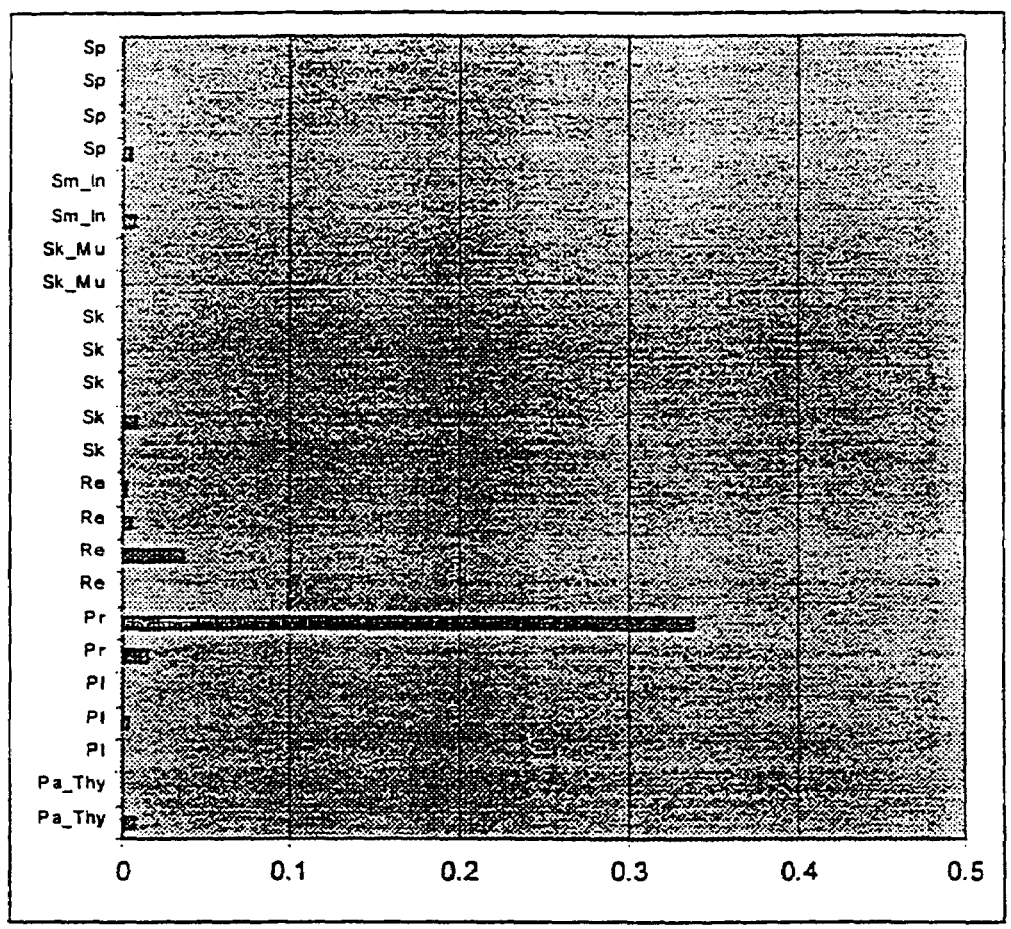

Figure 2D: Real-time PCR data of CASB618 expression in normal tissues (continued)
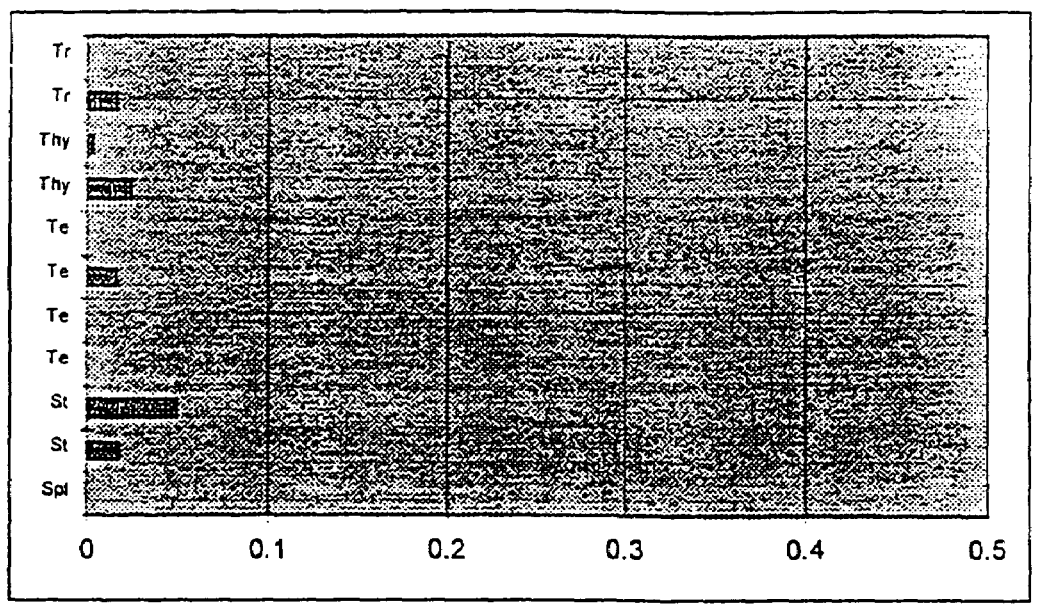

Figure 3: SDS-PAGE gel (12.5 %) of the *E. coli* AR120/pRIT15081 extract.
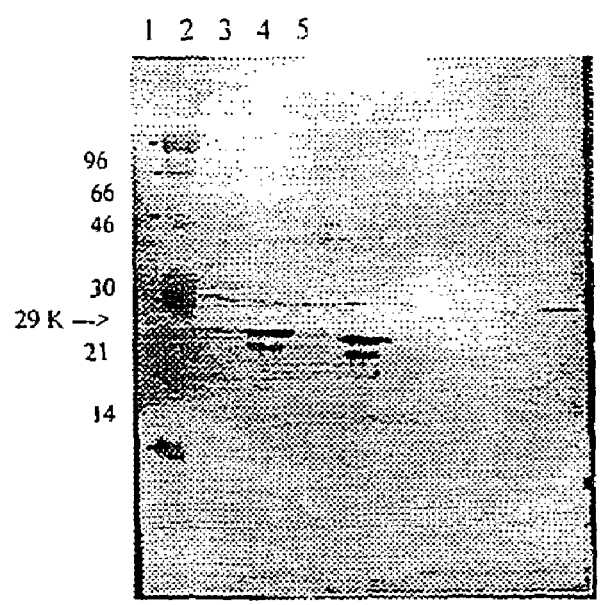

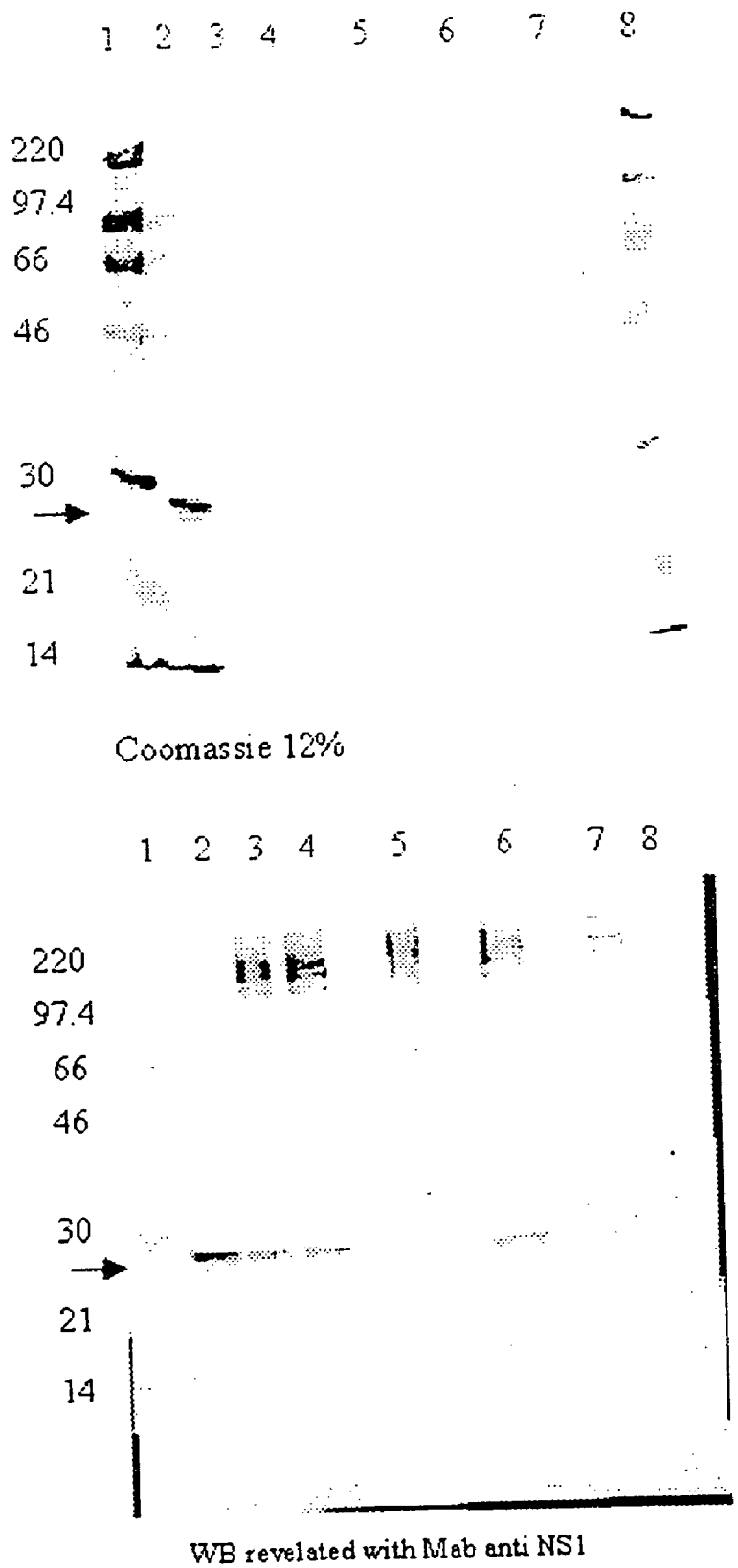
Figure 4: SDS-PAGE gels of purified CASB618

SEQUENCE LISTING

<160> NUMBER OF SEQ ID NOS: 77

<210> SEQ ID NO 1
<211> LENGTH: 1441
<212> TYPE: DNA
<213> ORGANISM: Human

<400> SEQUENCE: 1

```
aaagtaacgg ctacagacag tgagaaatag tttcgctcgc cggctagaaa aactctgtcg      60
gtaccaaccc cagagcgttg agagcagccc acctccacgc ttccttaacg gagaggtgca     120
ggactcgagac ttcaccagcc cactcggtcc cagccttgta cgcaaagaga cgccaaggac    180
gcgctctccc gcgtccaggc agccccagct tgctggcttg cctgcccgcc tgcgtgcagc    240
actcggccgg cgtgcagcat gacccgtgtgg aacggcgtac tgccttttta cccccagccc    300
cggcatgccg caggcttcag cgttccactg ctcatcgtta ttctagtgtt tttggctcta    360
gcagcaagct tcctgctcat cttgccgggg atccgtggcc actcgcgctg gttttggttg    420
gtgagagttc ttctcagtct gttcataggc gcagaaattg tggctgtgca cttcagtgca    480
gaatggttcg tgggtacagt gaacaccaac acatcctaca aagccttcag cgcagcgcgc    540
gttacagccc gtgtcggtct gctcgtgggc ctggagggca ttaatattac actcacaggg    600
accccagtgc atcagctgaa cgagaccatt gactacaacg agcagttcac ctggcgtctg    660
aaagagaatt acgccgcgga gtacgcgaac gcactggaga aggggctgcc ggacccagtg    720
ctctacctgg cggagaagtt cacaccgagt agcccttgcg gcctgtacca ccagtaccac    780
ctggcgggac actacgcctc ggccacgcta tgggtggcgt tctgcttctg gctcctctcc    840
aacgtgctgc tctccacgcc ggccccgctc tacggaggcc tggcactgct gaccaccgga    900
gccttcgcgc tcttcggggt cttcgccttg gcctccatct ctagcgtgcc gctctgcccg    960
ctccgcctag gctcctccgc gctcaccact cagtacggcg ccgccttctg ggtcacgctg   1020
gcaaccggcg tcctgtgcct cttcctcgga ggggccgtgg tgagtctcca gtatgttcgg   1080
cccagcgctc ttcgcaccct tctggaccaa agcgccaagg actgcagcca ggagagaggg   1140
ggctcacctc ttatcctcgg cgacccactg cacaagcagg ccgctctccc agacttaaaa   1200
tgtatcacca ctaacctgtg aggggaccc aatctggact ccttcccgc cttgggacat      1260
cgcaggccgg gaagcagtgc ccgccaggcc tgggccagga gagctccagg aagggcactg   1320
```

-continued agcgctgctg gcgcgaggcc tcggacatcc gcaggcacca gggaaagtct cctggggcga      1380
tctgtaaata aaccttttt tctttgttt tttaaaaaaa aaaaaaaaaa aaaaaaaaa         1440 a                                                                     1441

<210> SEQ ID NO 2
<211> LENGTH: 320
<212> TYPE: PRT
<213> ORGANISM: Human

<400> SEQUENCE: 2

Met Thr Leu Trp Asn Gly Val Leu Pro Phe Tyr Pro Gln Pro Arg His
 1               5                  10                  15

Ala Ala Gly Phe Ser Val Pro Leu Leu Ile Val Ile Leu Val Phe Leu
                20                  25                  30

Ala Leu Ala Ala Ser Phe Leu Leu Ile Leu Pro Gly Ile Arg Gly His
            35                  40                  45

Ser Arg Trp Phe Trp Leu Val Arg Val Leu Leu Ser Leu Phe Ile Gly
        50                  55                  60

Ala Glu Ile Val Ala Val His Phe Ser Ala Glu Trp Phe Val Gly Thr
65                  70                  75                  80

Val Asn Thr Asn Thr Ser Tyr Lys Ala Phe Ser Ala Ala Arg Val Thr
                85                  90                  95

Ala Arg Val Gly Leu Leu Val Gly Leu Glu Gly Ile Asn Ile Thr Leu
            100                 105                 110

Thr Gly Thr Pro Val His Gln Leu Asn Glu Thr Ile Asp Tyr Asn Glu
        115                 120                 125

Gln Phe Thr Trp Arg Leu Lys Glu Asn Tyr Ala Ala Glu Tyr Ala Asn
    130                 135                 140

Ala Leu Glu Lys Gly Leu Pro Asp Pro Val Leu Tyr Leu Ala Glu Lys
145                 150                 155                 160

Phe Thr Pro Ser Ser Pro Cys Gly Leu Tyr His Gln Tyr His Leu Ala
                165                 170                 175

Gly His Tyr Ala Ser Ala Thr Leu Trp Val Ala Phe Cys Phe Trp Leu
            180                 185                 190

Leu Ser Asn Val Leu Leu Ser Thr Pro Ala Pro Leu Tyr Gly Gly Leu
        195                 200                 205

Ala Leu Leu Thr Thr Gly Ala Phe Ala Leu Phe Gly Val Phe Ala Leu
    210                 215                 220

Ala Ser Ile Ser Ser Val Pro Leu Cys Pro Leu Arg Leu Gly Ser Ser
225                 230                 235                 240

Ala Leu Thr Thr Gln Tyr Gly Ala Ala Phe Trp Val Thr Leu Ala Thr
                245                 250                 255

Gly Val Leu Cys Leu Phe Leu Gly Gly Ala Val Val Ser Leu Gln Tyr
            260                 265                 270

Val Arg Pro Ser Ala Leu Arg Thr Leu Leu Asp Gln Ser Ala Lys Asp
        275                 280                 285

Cys Ser Gln Glu Arg Gly Gly Ser Pro Leu Ile Leu Gly Asp Pro Leu
    290                 295                 300

His Lys Gln Ala Ala Leu Pro Asp Leu Lys Cys Ile Thr Thr Asn Leu
305                 310                 315                 320

<210> SEQ ID NO 3
<211> LENGTH: 498
<212> TYPE: DNA
<213> ORGANISM: Human

<400> SEQUENCE: 3

```
ctctagcgtg ccgctctgcc cgctcccgcc taggctcctc cgcgctcacc actcagtacg    60
agcgccgcct tctgggtcac gctggcaacc ggcgtcctgt gcctcttcct cggaggggcc   120
gtggtgagtc tccagtatgt tcggcccagc gctcttcgca cccttctgga ccaaagcgcc   180
aaggactgca gccaggagag agggggctca cctcttatcc tcggcgaccc actgcacaag   240
caggccgctc tcccagactt aaaatgtatc accactaacc tgtgaggggg acccaatctg   300
gactccttcc ccgccttggg acatcgcagg ccgggaagca gtgcccgcca ggcctgggcc   360
aggagagctc caggaagggc actgagcgct gctggcgcga ggcctcggac atccgcaggc   420
accaggaaaa gtctcctggg gcgatctgta aataaacctt ttttctttt gtttttaaa    480
aaaaaataaa agtcgacc                                                 498
```

<210> SEQ ID NO 4
<211> LENGTH: 262
<212> TYPE: PRT
<213> ORGANISM: Human

<400> SEQUENCE: 4

```
Met Asp Pro Asn Thr Val Ser Ser Phe Gln Val Asp Cys Phe Leu Trp
  1               5                  10                  15

His Val Arg Lys Arg Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asp Ile Glu Thr Ala Thr Arg Ala Gly Lys Gln Ile
     50                  55                  60

Val Glu Arg Ile Leu Lys Glu Glu Ser Asp Glu Ala Leu Lys Met Thr
 65                  70                  75                  80

Met Glu Trp Phe Val Gly Thr Val Asn Thr Asn Thr Ser Tyr Lys Ala
                 85                  90                  95

Phe Ser Ala Ala Arg Val Thr Ala Arg Val Gly Leu Leu Val Gly Leu
            100                 105                 110

Glu Gly Ile Asn Ile Thr Leu Thr Gly Thr Pro Val His Gln Leu Asn
        115                 120                 125

Glu Thr Ile Asp Tyr Asn Glu Gln Phe Thr Trp Arg Leu Lys Glu Asn
    130                 135                 140

Tyr Ala Ala Glu Tyr Ala Asn Ala Leu Glu Lys Gly Leu Pro Asp Pro
145                 150                 155                 160

Val Leu Tyr Leu Ala Glu Lys Phe Thr Pro Ser Ser Pro Cys Gly Leu
                165                 170                 175

Tyr His Gln Tyr His Leu Ala Gly His Tyr Ala Ser Ala Thr Leu Trp
            180                 185                 190

Val Ala Phe Cys Phe Trp Leu Ser Asn Val Leu Leu Ser Thr Pro
        195                 200                 205

Ala Pro Leu Tyr Gly Gly Leu Ala Leu Leu Thr Thr Gly Ala Phe Ala
    210                 215                 220

Leu Phe Gly Val Phe Ala Leu Ala Ser Ile Ser Ser Val Pro Leu Cys
225                 230                 235                 240

Pro Leu Arg Leu Gly Ser Ser Ala Leu Thr Thr Gln Tyr Thr Ser Gly
                245                 250                 255

His His His His His His
            260
```

```
<210> SEQ ID NO 5
<211> LENGTH: 9
<212> TYPE: PRT
<213> ORGANISM: Human

<400> SEQUENCE: 5

Phe Leu Gly Gly Ala Val Val Ser Leu
  1               5

<210> SEQ ID NO 6
<211> LENGTH: 9
<212> TYPE: PRT
<213> ORGANISM: Human

<400> SEQUENCE: 6

Leu Leu Ile Val Ile Leu Val Phe Leu
  1               5

<210> SEQ ID NO 7
<211> LENGTH: 9
<212> TYPE: PRT
<213> ORGANISM: Human

<400> SEQUENCE: 7

Thr Leu Ala Thr Gly Val Leu Cys Leu
  1               5

<210> SEQ ID NO 8
<211> LENGTH: 9
<212> TYPE: PRT
<213> ORGANISM: Human

<400> SEQUENCE: 8

Pro Leu Tyr Gly Gly Leu Ala Leu Leu
  1               5

<210> SEQ ID NO 9
<211> LENGTH: 9
<212> TYPE: PRT
<213> ORGANISM: Human

<400> SEQUENCE: 9

Gly Leu Pro Asp Pro Val Leu Tyr Leu
  1               5

<210> SEQ ID NO 10
<211> LENGTH: 9
<212> TYPE: PRT
<213> ORGANISM: Human

<400> SEQUENCE: 10

Gly Leu Leu Val Gly Leu Glu Gly Ile
  1               5

<210> SEQ ID NO 11
<211> LENGTH: 9
<212> TYPE: PRT
<213> ORGANISM: Human

<400> SEQUENCE: 11

Trp Leu Val Arg Val Leu Leu Ser Leu
  1               5
```

```
<210> SEQ ID NO 12
<211> LENGTH: 9
<212> TYPE: PRT
<213> ORGANISM: Human

<400> SEQUENCE: 12

Phe Ile Gly Ala Glu Ile Val Ala Val
 1               5

<210> SEQ ID NO 13
<211> LENGTH: 9
<212> TYPE: PRT
<213> ORGANISM: Human

<400> SEQUENCE: 13

Cys Leu Phe Leu Gly Gly Ala Val Val
 1               5

<210> SEQ ID NO 14
<211> LENGTH: 9
<212> TYPE: PRT
<213> ORGANISM: Human

<400> SEQUENCE: 14

Val Leu Leu Ser Thr Pro Ala Pro Leu
 1               5

<210> SEQ ID NO 15
<211> LENGTH: 9
<212> TYPE: PRT
<213> ORGANISM: Human

<400> SEQUENCE: 15

Ser Leu Phe Ile Gly Ala Glu Ile Val
 1               5

<210> SEQ ID NO 16
<211> LENGTH: 9
<212> TYPE: PRT
<213> ORGANISM: Human

<400> SEQUENCE: 16

Leu Leu Thr Thr Gly Ala Phe Ala Leu
 1               5

<210> SEQ ID NO 17
<211> LENGTH: 9
<212> TYPE: PRT
<213> ORGANISM: Human

<400> SEQUENCE: 17

Gly Leu Glu Gly Ile Asn Ile Thr Leu
 1               5

<210> SEQ ID NO 18
<211> LENGTH: 9
<212> TYPE: PRT
<213> ORGANISM: Human

<400> SEQUENCE: 18

Leu Ala Ala Ser Phe Leu Leu Ile Leu
 1               5

<210> SEQ ID NO 19
<211> LENGTH: 9
```

```
<212> TYPE: PRT
<213> ORGANISM: Human

<400> SEQUENCE: 19

Phe Ala Leu Ala Ser Ile Ser Ser Val
1               5

<210> SEQ ID NO 20
<211> LENGTH: 9
<212> TYPE: PRT
<213> ORGANISM: Human

<400> SEQUENCE: 20

Phe Ala Leu Phe Gly Val Phe Ala Leu
1               5

<210> SEQ ID NO 21
<211> LENGTH: 9
<212> TYPE: PRT
<213> ORGANISM: Human

<400> SEQUENCE: 21

Leu Leu Ser Asn Val Leu Leu Ser Thr
1               5

<210> SEQ ID NO 22
<211> LENGTH: 9
<212> TYPE: PRT
<213> ORGANISM: Human

<400> SEQUENCE: 22

Tyr Ala Ala Glu Tyr Ala Asn Ala Leu
1               5

<210> SEQ ID NO 23
<211> LENGTH: 9
<212> TYPE: PRT
<213> ORGANISM: Human

<400> SEQUENCE: 23

Ala Leu Ala Ala Ser Phe Leu Leu Ile
1               5

<210> SEQ ID NO 24
<211> LENGTH: 9
<212> TYPE: PRT
<213> ORGANISM: Human

<400> SEQUENCE: 24

Phe Leu Ala Leu Ala Ala Ser Phe Leu
1               5

<210> SEQ ID NO 25
<211> LENGTH: 9
<212> TYPE: PRT
<213> ORGANISM: Human

<400> SEQUENCE: 25

Ser Val Pro Leu Leu Ile Val Ile Leu
1               5

<210> SEQ ID NO 26
<211> LENGTH: 9
<212> TYPE: PRT
<213> ORGANISM: Human
```

```
<400> SEQUENCE: 26

His Leu Ala Gly His Tyr Ala Ser Ala
 1               5

<210> SEQ ID NO 27
<211> LENGTH: 9
<212> TYPE: PRT
<213> ORGANISM: Human

<400> SEQUENCE: 27

Leu Thr Gly Thr Pro Val His Gln Leu
 1               5

<210> SEQ ID NO 28
<211> LENGTH: 9
<212> TYPE: PRT
<213> ORGANISM: Human

<400> SEQUENCE: 28

Ala Arg Val Gly Leu Leu Val Gly Leu
 1               5

<210> SEQ ID NO 29
<211> LENGTH: 9
<212> TYPE: PRT
<213> ORGANISM: Human

<400> SEQUENCE: 29

Ser Ala Ala Arg Val Thr Ala Arg Val
 1               5

<210> SEQ ID NO 30
<211> LENGTH: 9
<212> TYPE: PRT
<213> ORGANISM: Human

<400> SEQUENCE: 30

Ser Ala Glu Trp Phe Val Gly Thr Val
 1               5

<210> SEQ ID NO 31
<211> LENGTH: 9
<212> TYPE: PRT
<213> ORGANISM: Human

<400> SEQUENCE: 31

Val Ile Leu Val Phe Leu Ala Leu Ala
 1               5

<210> SEQ ID NO 32
<211> LENGTH: 9
<212> TYPE: PRT
<213> ORGANISM: Human

<400> SEQUENCE: 32

Ala Ala Leu Pro Asp Leu Lys Cys Ile
 1               5

<210> SEQ ID NO 33
<211> LENGTH: 9
<212> TYPE: PRT
<213> ORGANISM: Human

<400> SEQUENCE: 33
```

```
Ile Leu Gly Asp Pro Leu His Lys Gln
1               5
```

<210> SEQ ID NO 34
<211> LENGTH: 9
<212> TYPE: PRT
<213> ORGANISM: Human

<400> SEQUENCE: 34

```
Val Leu Cys Leu Phe Leu Gly Gly Ala
1               5
```

<210> SEQ ID NO 35
<211> LENGTH: 9
<212> TYPE: PRT
<213> ORGANISM: Human

<400> SEQUENCE: 35

```
Ala Leu Phe Gly Val Phe Ala Leu Ala
1               5
```

<210> SEQ ID NO 36
<211> LENGTH: 9
<212> TYPE: PRT
<213> ORGANISM: Human

<400> SEQUENCE: 36

```
Gly Leu Ala Leu Leu Thr Thr Gly Ala
1               5
```

<210> SEQ ID NO 37
<211> LENGTH: 9
<212> TYPE: PRT
<213> ORGANISM: Human

<400> SEQUENCE: 37

```
Leu Ile Leu Pro Gly Ile Arg Gly His
1               5
```

<210> SEQ ID NO 38
<211> LENGTH: 9
<212> TYPE: PRT
<213> ORGANISM: Human

<400> SEQUENCE: 38

```
His Ala Ala Gly Phe Ser Val Pro Leu
1               5
```

<210> SEQ ID NO 39
<211> LENGTH: 9
<212> TYPE: PRT
<213> ORGANISM: Protein

<400> SEQUENCE: 39

```
Asp Leu Lys Cys Ile Thr Thr Asn Leu
1               5
```

<210> SEQ ID NO 40
<211> LENGTH: 9
<212> TYPE: PRT
<213> ORGANISM: Human

<400> SEQUENCE: 40

```
Pro Leu Arg Leu Gly Ser Ser Ala Leu
```

```
<210> SEQ ID NO 41
<211> LENGTH: 9
<212> TYPE: PRT
<213> ORGANISM: Human

<400> SEQUENCE: 41

Ala Leu Leu Thr Thr Gly Ala Phe Ala
 1               5

<210> SEQ ID NO 42
<211> LENGTH: 9
<212> TYPE: PRT
<213> ORGANISM: Human

<400> SEQUENCE: 42

Ile Val Ile Leu Val Phe Leu Ala Leu
 1               5

<210> SEQ ID NO 43
<211> LENGTH: 9
<212> TYPE: PRT
<213> ORGANISM: Human

<400> SEQUENCE: 43

Ala Ala Gly Phe Ser Val Pro Leu Leu
 1               5

<210> SEQ ID NO 44
<211> LENGTH: 9
<212> TYPE: PRT
<213> ORGANISM: Human

<400> SEQUENCE: 44

Val Leu Tyr Leu Ala Glu Lys Phe Thr
 1               5

<210> SEQ ID NO 45
<211> LENGTH: 9
<212> TYPE: PRT
<213> ORGANISM: Human

<400> SEQUENCE: 45

Thr Gln Tyr Gly Ala Ala Phe Trp Trp
 1               5

<210> SEQ ID NO 46
<211> LENGTH: 9
<212> TYPE: PRT
<213> ORGANISM: Human

<400> SEQUENCE: 46

Trp Val Ala Phe Cys Phe Trp Leu Leu
 1               5

<210> SEQ ID NO 47
<211> LENGTH: 10
<212> TYPE: PRT
<213> ORGANISM: Human

<400> SEQUENCE: 47

Ala Leu Ala Ala Ser Phe Leu Leu Ile Leu
 1               5                  10
```

<210> SEQ ID NO 48
<211> LENGTH: 10
<212> TYPE: PRT
<213> ORGANISM: Human

<400> SEQUENCE: 48

Ala Leu Ala Ser Ile Ser Ser Val Pro Leu
1               5                   10

<210> SEQ ID NO 49
<211> LENGTH: 10
<212> TYPE: PRT
<213> ORGANISM: Human

<400> SEQUENCE: 49

Thr Leu Thr Gly Thr Pro Val His Gln Leu
1               5                   10

<210> SEQ ID NO 50
<211> LENGTH: 10
<212> TYPE: PRT
<213> ORGANISM: Human

<400> SEQUENCE: 50

Ala Leu Leu Thr Thr Gly Ala Phe Ala Leu
1               5                   10

<210> SEQ ID NO 51
<211> LENGTH: 10
<212> TYPE: PRT
<213> ORGANISM: Human

<400> SEQUENCE: 51

Pro Leu Leu Ile Val Ile Leu Val Phe Leu
1               5                   10

<210> SEQ ID NO 52
<211> LENGTH: 10
<212> TYPE: PRT
<213> ORGANISM: Human

<400> SEQUENCE: 52

Tyr Val Arg Pro Ser Ala Leu Arg Thr Leu
1               5                   10

<210> SEQ ID NO 53
<211> LENGTH: 10
<212> TYPE: PRT
<213> ORGANISM: Human

<400> SEQUENCE: 53

Leu Phe Leu Gly Gly Ala Val Val Ser Leu
1               5                   10

<210> SEQ ID NO 54
<211> LENGTH: 10
<212> TYPE: PRT
<213> ORGANISM: Human

<400> SEQUENCE: 54

Ser Ile Ser Ser Val Pro Leu Cys Pro Leu
1               5                   10

<210> SEQ ID NO 55

```
<211> LENGTH: 10
<212> TYPE: PRT
<213> ORGANISM: Human

<400> SEQUENCE: 55

Leu Leu Ser Leu Phe Ile Gly Ala Glu Ile
1               5                   10

<210> SEQ ID NO 56
<211> LENGTH: 10
<212> TYPE: PRT
<213> ORGANISM: Human

<400> SEQUENCE: 56

Trp Leu Leu Ser Asn Val Leu Leu Ser Thr
1               5                   10

<210> SEQ ID NO 57
<211> LENGTH: 10
<212> TYPE: PRT
<213> ORGANISM: Human

<400> SEQUENCE: 57

Leu Phe Ile Gly Ala Glu Ile Val Ala Val
1               5                   10

<210> SEQ ID NO 58
<211> LENGTH: 10
<212> TYPE: PRT
<213> ORGANISM: Human

<400> SEQUENCE: 58

Phe Leu Ala Leu Ala Ala Ser Phe Leu Leu
1               5                   10

<210> SEQ ID NO 59
<211> LENGTH: 10
<212> TYPE: PRT
<213> ORGANISM: Human

<400> SEQUENCE: 59

His Ala Ala Gly Phe Ser Val Pro Leu Leu
1               5                   10

<210> SEQ ID NO 60
<211> LENGTH: 10
<212> TYPE: PRT
<213> ORGANISM: Human

<400> SEQUENCE: 60

Ser Leu Gln Tyr Val Arg Pro Ser Ala Leu
1               5                   10

<210> SEQ ID NO 61
<211> LENGTH: 10
<212> TYPE: PRT
<213> ORGANISM: Human

<400> SEQUENCE: 61

Val Leu Cys Leu Phe Leu Gly Gly Ala Val
1               5                   10

<210> SEQ ID NO 62
<211> LENGTH: 10
<212> TYPE: PRT
```

<213> ORGANISM: Human

<400> SEQUENCE: 62

Val Thr Leu Ala Thr Gly Val Leu Cys Leu
1               5                   10

<210> SEQ ID NO 63
<211> LENGTH: 10
<212> TYPE: PRT
<213> ORGANISM: Protein

<400> SEQUENCE: 63

Leu Leu Val Gly Leu Glu Gly Ile Asn Ile
1               5                   10

<210> SEQ ID NO 64
<211> LENGTH: 10
<212> TYPE: PRT
<213> ORGANISM: Protein

<400> SEQUENCE: 64

Leu Ile Val Ile Leu Val Phe Leu Ala Leu
1               5                   10

<210> SEQ ID NO 65
<211> LENGTH: 10
<212> TYPE: PRT
<213> ORGANISM: Protein

<400> SEQUENCE: 65

Leu Leu Ile Val Ile Leu Val Phe Leu Ala
1               5                   10

<210> SEQ ID NO 66
<211> LENGTH: 10
<212> TYPE: PRT
<213> ORGANISM: Human

<400> SEQUENCE: 66

Leu Ile Leu Gly Asp Pro Leu His Lys Gln
1               5                   10

<210> SEQ ID NO 67
<211> LENGTH: 10
<212> TYPE: PRT
<213> ORGANISM: Human

<400> SEQUENCE: 67

Thr Leu Trp Val Ala Phe Cys Phe Trp Leu
1               5                   10

<210> SEQ ID NO 68
<211> LENGTH: 10
<212> TYPE: PRT
<213> ORGANISM: Human

<400> SEQUENCE: 68

Gly Leu Pro Asp Pro Val Leu Tyr Leu Ala
1               5                   10

<210> SEQ ID NO 69
<211> LENGTH: 10
<212> TYPE: PRT
<213> ORGANISM: Human

-continued

<400> SEQUENCE: 69

Ala Leu Glu Lys Gly Leu Pro Asp Pro Val
1               5                   10

<210> SEQ ID NO 70
<211> LENGTH: 10
<212> TYPE: PRT
<213> ORGANISM: Human

<400> SEQUENCE: 70

Thr Ala Arg Val Gly Leu Leu Val Gly Leu
1               5                   10

<210> SEQ ID NO 71
<211> LENGTH: 10
<212> TYPE: PRT
<213> ORGANISM: Human

<400> SEQUENCE: 71

Phe Ser Ala Glu Trp Phe Val Gly Thr Val
1               5                   10

<210> SEQ ID NO 72
<211> LENGTH: 10
<212> TYPE: PRT
<213> ORGANISM: Human

<400> SEQUENCE: 72

Leu Ala Gly His Tyr Ala Ser Ala Thr Leu
1               5                   10

<210> SEQ ID NO 73
<211> LENGTH: 10
<212> TYPE: PRT
<213> ORGANISM: Human

<400> SEQUENCE: 73

Lys Gly Leu Pro Asp Pro Val Leu Tyr Leu
1               5                   10

<210> SEQ ID NO 74
<211> LENGTH: 10
<212> TYPE: PRT
<213> ORGANISM: Human

<400> SEQUENCE: 74

Gly Leu Glu Gly Ile Asn Ile Thr Leu Thr
1               5                   10

<210> SEQ ID NO 75
<211> LENGTH: 10
<212> TYPE: PRT
<213> ORGANISM: Human

<400> SEQUENCE: 75

Phe Trp Leu Val Arg Val Leu Leu Ser Leu
1               5                   10

<210> SEQ ID NO 76
<211> LENGTH: 10
<212> TYPE: PRT
<213> ORGANISM: Human

<400> SEQUENCE: 76

```
Ser Val Pro Leu Leu Ile Val Ile Leu Val
1               5                   10

<210> SEQ ID NO 77
<211> LENGTH: 10
<212> TYPE: PRT
<213> ORGANISM: Human

<400> SEQUENCE: 77

Ala Val His Phe Ser Ala Glu Trp Phe Val
1               5                   10
```

CASB618 POLYNUCLEOTIDES AND POLYPEPTIDES AND THEIR USE

This application is a continuation application of U.S. application Ser. No. 09/936,456, filed Jan. 14, 2002 now abandoned, which claims benefit to International Application PCT/EP00/02048, filed Sep. 14, 2000, which claims priority to British provisional applications GB 9905607.9 filed May 11, 1999 and GB 9920590.8, filed Sep. 1, 1999.

FIELD OF THE INVENTION

The present invention relates to polynucleotides, herein referred to as CASB618 polynucleotides, polypeptides encoded thereby (referred to herein as CASB618 polypeptides), recombinant materials and methods for their production. In another aspect, the invention relates to methods for using such polypeptides and polynucleotides, including the treatment of cancer in particular in the treatment of colon cancer, and autoimmune diseases and other related conditions. In a further aspect, the invention relates to methods for identifying agonists and antagonists/inhibitors using the materials provided by the invention, and treating conditions associated with CASB618 polypeptide imbalance with the identified compounds. In a still further aspect, the invention relates to diagnostic assays for detecting diseases associated with inappropriate CASB618 polypeptide activity or levels.

BACKGROUND OF THE INVENTION

Polypeptides and polynucleotides of the present invention are important immunogens for specific prophylactic or therapeutic immunization against tumours, because they are specifically expressed or highly over-expressed in tumours compared to normal cells and can be targeted by antigen-specific immune mechanisms leading to the destruction of the tumour cell. They can also be used to diagnose the occurrence of tumour cells. Furthermore, their inappropriate expression in certain circumstances can cause an induction of autoimmune, inappropriate immune responses, which can be corrected through appropriate vaccination using the same polypeptides or polynucleotides. In this respect the most important biological properties are the antigenic and immunogenic activities of the polypeptide of the present invention. A polypeptide of the present invention may also exhibit at least one other biological activity of a CASB618 polypeptide, which could qualify it as a target for therapeutic or prophylactic intervention different from that linked to its use as an immunotherapeutic.

Functional genomics relies heavily on high-throughput DNA sequencing technologies and the various tools of bioinformatics to identify gene sequences of potential interest from the many molecular biology databases now available. cDNA libraries enriched for genes of relevance to a particular tissue or physiological situation can be constructed using recently developed subtractive cloning strategies. Furthermore, cDNAs found in libraries of certain tissues and not others can be identified using appropriate electronic screening methods.

High throughput genome- or gene-based biology allows new approaches to the identification and cloning of target genes for useful immune responses for the prevention and vaccine therapy of diseases such as cancer and autoimmunity.

SUMMARY OF THE INVENTION

In a first aspect, the present invention relates to CASB618 polypeptides. Such peptides include isolated polypeptides comprising an amino acid sequence which has at least 70% identity, preferably at least 80% identity, more preferably at least 90% identity, yet more preferably at least 95% identity, most preferably at least 97-99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity, preferably at least 80% identity, more preferably at least 90% identity, yet more preferably at least 95% identity, most preferably at least 97-99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

The invention also provides an immunogenic fragment of a CASB618 polypeptide, that is a contiguous portion of the CASB618 polypeptide which has the same or similar immunogenic properties to the polypeptide comprising the amino acid seqeunce of SEQ ID NO:2. That is to say, the fragment (if necessary when coupled to a carrier) is capable of raising an immune response which recognises the CASB618 polypeptide. Such an immunogenic fragment may include, for example, the CASB618 polypeptide lacking an N-terminal leader sequence, a transmembrane domain or a C-terminal anchor domain. In a preferred aspect the immunogenic fragment of CASB618 according to the invention comprises substantially all of the extracellular domain of a polypeptide which has at least 70% identity, preferably at least 80% identity, more preferably at least 90% identity, yet more preferably at least 95% identity, most preferably at least 97-99% identity, to that of SEQ ID NO:2 over the entire length of SEQ ID NO:2.

Peptide fragments incorporating an epitope of CASB618 typically will comprise at least 7, preferably 9 or 10 contiguous amino acids from SEQ ID NO:2. Preferred epitopes are shown in SEQ ID NO:5 to SEQ ID NO:77.

Peptides that incorporate these epitopes form a preferred aspect of the present invention. Mimotopes which have the same characteristics as these epitopes, and immunogens comprising such mimotopes which generate an immune response which cross-react with an epitope in the context of the CASB618 molecule, also form part of the present invention.

BRIEF DESCRIPTION OF THE FIGURES

FIG. 1 graphs expression levels of CASB618 in matched colon normal and tumoral samples. The values are given in equivalent actin level. N refers to normal colon samples, T refers to tumoral colon samples.

FIG. 2A graphs real-time PCR results for CASB618 expression in normal tissues, where CO indicates colon; CE indicates cervix; Bra indicates brain; Bo Ma indicates bone marrow; Bl indicates bladder; Ao indicates aorta; and Ad Gl indicates adrenal gland.

FIG. 2B graphs real-time PCR results for CASB618 expression in normal tissues, where OV indicates ovary; Oe indicates Oesophagus; Ly No indicates lymph node; Lu indicates lung; Li indicates liver; Ki indicates kidney, Il indicates ileum; He indicates heart and Fa Tu indicates fallopian tube.

FIG. 2C graphs real-time PCR results for CASB618 expression in normal tissues, where Sp indicates spleen; Sm In indicates small intestine; Sk Mu indicates skeletal muscle;

Sk indicates skin; Re indicates rectum; Pr indicates prostate; Pl indicates placenta; Pa Thy indicates parathyroid gland.

FIG. 2D graphs real-time PCR results for CASB618 expression in normal tissues, where Tr indicates trachea; Thy indicates thyroid; Te indicates testis; St indicates stomach and Spl indicates spleen.

FIG. 3 shows an SDS-PAGE gel (12.5%) of the *E. coli* AR 120/pRIT 15081 extract, with or without induction with nalidixic acid; revealed with monoclonal antibody anti-NS1. Lane 1 is the molecular weight marker; Lane 2 is *E. coli* AR120/pRIT 15081 3 hours, no induction; Lane 3 shows the *E. coli* AR120/pRIT 15081 3 hours, induced; Lane 4 shows the *E. coli* AR120/pRIT 15081 4 hours 30 minutes, no induction; Lane 5 shows the *E. coli* AR120/pRIT 15081 4 hours 30 minutes, induced.

FIG. 4 shows SDS-PAGE gels of purified CASB168, visualized using Coomassie 12% stain (top panel) and using Western Blot with anti-NS1 monoclonal antibody (lower panel). Lanes 1 and 8 show the molecular weight marker; lane 2 shows the lysed cell pellet; lane 3 shows the three purified proteins before dialysis; lane 4 shows the purified dialysed protein; lane 6 shows the purified dialysed protein 0.22 ptm.

DETAILED DESCRIPTION

The present invention, therefore, includes isolated peptides encompassing these epitopes themselves, and any mimotope thereof. The meaning of mimotope is defined as an entity which is sufficiently similar to the native CASB618 epitope so as to be capable of being recognised by antibodies which recognise the native molecule; (Gheysen, H. M., et al., 1986, Synthetic peptides as antigens. Wiley, Chichester, Ciba foundation symposium 119, p 130-149; Gheysen, H. M., 1986, Molecular Immunology, 23,7, 709-715); or are capable of raising antibodies, when coupled to a suitable carrier, which antibodies cross-react with the native molecule.

Peptide mimotopes of the above-identified epitopes may be designed for a particular purpose by addition, deletion or substitution of elected amino acids. Thus, the peptides of the present invention may be modified for the purposes of ease of conjugation to a protein carrier. For example, it may be desirable for some chemical conjugation methods to include a terminal cysteine to the epitope. In addition it may be desirable for peptides conjugated to a protein carrier to include a hydrophobic terminus distal from the conjugated terminus of the peptide, such that the free unconjugated end of the peptide remains associated with the surface of the carrier protein. This reduces the conformational degrees of freedom of the peptide, and thus increases the probability that the peptide is presented in a conformation which most closely resembles that of the peptide as found in the context of the whole molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide. Those skilled in the art will realise that such modified peptides, or mimotopes, could be a wholly or partly non-peptide mimotope wherein the constituent residues are not necessarily confined to the 20 naturally occurring amino acids. In addition, these may be cyclised by techniques known in the art to constrain the peptide into a conformation that closely resembles its shape when the peptide sequence is in the context of the whole molecule. A preferred method of cyclising a peptide comprises the addition of a pair of cysteine residues to allow the formation of a disulphide bridge.

Further, those skilled in the art will realise that mimotopes or immunogens of the present invention may be larger than the above-identified epitopes, and as such may comprise the sequences disclosed herein. Accordingly, the mimotopes of the present invention may consist of addition of N and/or C terminal extensions of a number of other natural residues at one or both ends. The peptide mimotopes may also be retro sequences of the natural sequences, in that the sequence orientation is reversed; or alternatively the sequences may be entirely or at least in part comprised of D-stereo isomer amino acids (inverso sequences). Also, the peptide sequences may be retro-inverso in character, in that the sequence orientation is reversed and the amino acids are of the D-stereoisomer form. Such retro or retro-inverso peptides have the advantage of being non-self, and as such may overcome problems of self-tolerance in the immune system.

Alternatively, peptide mimotopes may be identified using antibodies which are capable themselves of binding to the epitopes of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native peptide. This approach may have significant advantages by allowing the possibility of identifying a peptide with enhanced immunogenic properties, or may overcome any potential self-antigen tolerance problems which may be associated with the use of the native peptide sequence. Additionally this technique allows the identification of a recognition pattern for each native-peptide in terms of its shared chemical properties amongst recognised mimotope sequences.

The covalent coupling of the peptide to the immunogenic carrier can be carried out in a manner well known in the art, Thus, for example, for direct covalent coupling it is possible to utilise a carbodiimide, glutaraldehyde or (N-[γ-maleimidobutyryloxy] succinimide ester, utilising common commercially available heterobifunctional linkers such as CDAP and SPDP (using manufacturers instructions). After the coupling reaction, the immunogen can easily be isolated and purified by means of a dialysis method, a gel filtration method, a fractionation method etc.

The types of carriers used in the immunogens of the present invention will be readily known to the man skilled in the art. The function of the carrier is to provide cytokine help in order to help induce an immune response against the peptide. A non-exhaustive list of carriers which may be used in the present invention include: Keyhole limpet Haemocyanin (KLH), serum albumins such as bovine serum albumin (BSA), inactivated bacterial toxins such as tetanus or diptheria toxins (TT and DT), or recombinant fragments thereof (for example, Domain 1 of Fragment C of TT, or the translocation domain of DT), or the purified protein derivative of tuberculin (PPD). Alternatively the mimotopes or epitopes may be directly conjugated to liposome carriers, which may additionally comprise immunogens capable of providing T-cell help. Preferably the ratio of mimotopes to carrier is in the order of 1:1 to 20:1, and preferably each carrier should carry between 3-15 peptides.

In an embodiment of the invention a preferred carrier is Protein D from *Haemophilus influenzae* (EP 0 594 610 B1). Protein D is an IgD-binding protein from *Haemophilus influenzae* and has been patented by Forsgren (WO 91/18926, granted EP 0 594 610 B1). In some circumstances, for example in recombinant immunogen expression systems it may be desirable to use fragments of protein D, for example Protein D ⅓$^{rd}$ (comprising the N-terminal 100-110 amino acids of protein D (GB 9717953.5)).

Another preferred method of presenting the peptides of the present invention is in the context of a recombinant fusion molecule. For example, EP 0 421 635 B describes the use of chimaeric hepadnavirus core antigen particles to present foreign peptide sequences in a virus-like particle. As such, immunogens of the present invention may comprise peptides presented in chimaeric particles consisting of hepatitis B core antigen. Additionally, the recombinant fusion proteins may comprise the mimotopes of the present invention and a carrier protein, such as NS1 of the influenza virus. For any recombinantly expressed protein which forms part of the present invention, the nucleic acid which encodes said immunogen also forms an aspect of the present invention.

Peptides used in the present invention can be readily synthesised by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989). Alternatively, the peptides may be produced by recombinant methods, including expressing nucleic acid molecules encoding the mimotopes in a bacterial or mammalian cell line, followed by purification of the expressed mimotope. Techniques for recombinant expression of peptides and proteins are known in the art, and are described in Maniatis, T., Fritsch, E. F. and Sambrook et al., *Molecular cloning, a laboratory manual*, 2nd Ed.; Cold Spring Harbor Laboratory Press, Cold Spring Harbor, N.Y. (1989).

The polypeptides or immunogenic fragment of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins.

Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenza* B and the non-structural protein from influenzae virus, NS1 (hemagglutinin). Another immunological fusion partner is the protein known as LYTA. Preferably the C terminal portion of the molecule is used. Lyta is derived from *Streptococcus pneumoniae* which synthesize an N-acetyl-L-alanine amidase, amidase LYTA, (coded by the lytA gene {Gene, 43 (1986) page 265-272} an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at its amino terminus has been described {Biotechnology: 10, (1992) page 795-798}. It is possible to use the repeat portion of the Lyta molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr, among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to CASB618 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard, polypeptides which have at least 97% identity are highly preferred, whilst those with at least 98-99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, over the entire coding region. In this regard, polynucleotides which have at least 97% identity are highly preferred, whilst those with at least 98-99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98-99% identity are more highly preferred, and those with at least 99% identity are most highly preferred. Such polynucleotides include a polynucleotide comprising the polynucleotide of SEQ ID NO:1 as well as the polynucleotide of SEQ ID NO:1. Said polynucleotide can be inserted in a suitable plasmid or recombinant microrganism vector and used for immunization (see for example Wolff et. al., Science 247:1465-1468 (1990); Corr et. al., J. Exp. Med. 184:1555-1560 (1996); Doe et. al., Proc. Natl. Acad. Sci. 93:8578-8583 (1996)). The invention also provides polynucleotides which are complementary to all the above described polynucleotides.

The invention also provides a fragment of a CASB618 polynucleotide which when administered to a subject has the same immunogenic properties as the polynucleotide of SEQ ID NO:1.

The invention also provides a polynucleotide encoding an immunological fragment of a CASB618 polypeptide as hereinbefore defined.

The nucleotide sequence of SEQ ID NO:1 shows homology with *Homo sapiens* chromosome 15 clone 163_P_10 map 15 (accession GB_HTG4:AC009700). The nucleotide sequence of SEQ ID NO:1 is a cDNA sequence and comprises a polypeptide encoding sequence (nucleotide 259 to 1219) encoding a polypeptide of 320 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is not related to any other protein of known function, except to *Caenorhabditis elegans* hypothetical 42.1 kd protein c06e1.3 (accession P34298).

Preferred polypeptides and polynucleotides of the present invention are expected to have, inter alia, similar biological functions/properties to their homologous polypeptides and polynucleotides. Furthermore, preferred polypeptides, immunological fragments and polynucleotides of the present invention have at least one activity of either SEQ ID NO:1 or SEQ ID NO:2, as appropriate.

The present invention also relates to partial or other incomplete polynucleotide and polypeptide sequences which were first identified prior to the determination of the corresponding full length sequences of SEQ ID NO:1 and SEQ ID NO:2.

Accordingly, in a further aspect the present invention provides for an isolated polynucleotide which:
(a) comprises a nucleotide sequence which has at least 70% identity, preferably at least 80% identity, more preferably at least 90% identity, yet more preferably at least 95% identity, even more preferably at least 97-99% identity to SEQ ID NO:3 over the entire length of SEQ ID NO:3;
(b) has a nucleotide sequence which has at least 70% identity, preferably at least 80% identity, more preferably at least 90% identity, yet more preferably at least 95% identity, even more preferably at least 97-99% identity, to SEQ ID NO:1 over the entire length of SEQ ID NO:3;
(c) the polynucleotide of SEQ ID NO:3.

The nucleotide sequence of SEQ ID NO:3 is derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 is therefore subject to the same inherent limitations in sequence accuracy.

Polynucleotides of the present invention may be obtained, using standard cloning and screening techniques, from a cDNA library derived from mRNA in cells of human colon cancer, lung cancer, uterine cancer, and fetal tissues (for example Sambrook et al., Molecular Cloning: A Laboratory Manual, $2^{nd}$ Ed., Cold Spring harbor Laboratory Press, Cold Spring harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821-824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides. In particular, polypeptides or polynucleotides derived from sequences from homologous animal origin could be used as immunogens to obtain a cross-reactive immune response to the human gene.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is short at the 5' end of the cDNA.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to an expression system which comprises a polynucleotide of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Preferably the proteins of the invention are coexpressed with thioredoxin in trans (TIT). Coexpression of thioredoxin in trans versus in cis is preferred to keep antigen free of thioredoxin without the need for protease. Thioredoxin coexpression eases the solubilisation of the proteins of the invention. Thioredoxin coexpression has also a significant impact on protein purification yield, on purified-protein solubility and quality.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems. e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), *Listeria, Salmonella, Shigella*, BCG. These viruses and bacteria can be virulent, or attenuated in various ways in order to obtain live vaccines. Such live vaccines also form part of the invention.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

Another important aspect of the invention relates to a method for inducing, re-inforcing or modulating an immunological response in a mammal which comprises inoculating the mammal with a fragment or the entire polypeptide or polynucleotide of the invention, adequate to produce antibody and/or T cell immune response for prophylaxis or for therapeutic treatment of cancer and autoimmune disease and related conditions. Yet another aspect of the invention relates to a method of inducing, reinforcing or modulating immunological response in a mammal which comprises, delivering a polypeptide of the present invention via a vector or cell directing expression of the polynucleotide and coding for the polypeptide in vivo in order to induce such an immunological response to produce immune responses for prophylaxis or treatment of said mammal from diseases.

A further aspect of the invention relates to an immunological/vaccine formulation (composition) which, when introduced into a mammalian host, induces, re-inforces or modulates an immunological response in that mammal to a polypeptide of the present invention wherein the composition comprises a polypeptide or polynucleotide of the invention or an immunological fragment thereof as herein before defined. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

A further aspect of the invention relates to the in vitro induction of immune responses to a fragment or the entire polypeptide or polynucleotide of the present invention or a molecule comprising the polypeptide or polynucleotide of the present invention, using cells from the immune system of a mammal, and reinfusing these activated immune cells of the mammal for the treatment of disease. Activation of the cells from the immune system is achieved by in vitro incubation with the entire polypeptide or polynucleotide of the present invention or a molecule comprising the polypeptide or polynucleotide of the present invention in the presence or absence of various immunomodulator molecules. A further aspect of the invention relates to the immunization of a mammal by administration of antigen presenting cells modified by in vitro loading with part or the entire polypeptide of the present invention or a molecule comprising the polypeptide of the present invention and administered in vivo in an immunogenic way. Alternatively, antigen presenting cells can be transfected in vitro with a vector containing a fragment or the entire polynucleotide of the present invention or a molecule comprising the polynucleotide of the present invention, such as to express the corresponding polypeptide, and administered in vivo in an immunogenic way.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) TH1 and TH2 *cells: different patterns of lymphokine secretion lead to different functional properties. Annual Review of Immunology,* 7, p 145-173). Traditionally, TH1-type responses are associated with the production of the INF-$\gamma$ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype. Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454).

3D-MPL will be present in the range of 10 $\mu$g-100 $\mu$g preferably 25-50 $\mu$g per dose wherein the antigen will typically be present in a range 2-50 $\mu$g per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response-include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

This invention also relates to the use of polynucleotides, in the form of primers derived from the polynucleotides of the present invention, and of polypeptides, in the form of antibodies or reagents specific for the polypeptide of the present invention, as diagnostic reagents.

The identification of genetic or biochemical markers in blood or tissues that will enable the detection of very early changes along the carcinogenesis pathway will help in determining the best treatment for the patient. Surrogate tumour markers, such as polynucleotide expression, can be used to diagnose different forms and states of cancer. The identification of expression levels of the polynucleotides of the invention will be useful in both the staging of the cancerous disorder and grading the nature of the cancerous tissue. The staging process monitors the advancement of the cancer and is determined on the presence or absence of malignant tissue in the areas biopsied. The polynucleotides of the invention can help to perfect the staging process by identifying markers for the aggresivity of a cancer, for example the presence in different areas of the body. The grading of the cancer describes how closely a tumour resembles normal tissue of its same type and is assessed by its cell morphology and other markers of differentiation. The polynucleotides of the invention can be useful in determining the tumour grade as they can help in the determination of the differentiation status of the cells of a tumour.

The diagnostic assays offer a process for diagnosing or determining a susceptibility to cancers, autoimmune disease and related conditions through diagnosis by methods comprising determining from a sample derived from a subject an abnormally decreased or increased level of polypeptide or mRNA. This method of diagnosis is known as differential expression. The expression of a particular gene is compared between a diseased tissue and a normal tissue. A difference between the polynucleotide-related gene, mRNA, or protein in the two tissues is compared, for example in molecular weight, amino acid or nucleotide sequence, or relative abundance, indicates a change in the gene, or a gene which regulates it, in the tissue of the human that was suspected of being diseased.

Decreased or increased expression can be measured at the RNA level. PolyA RNA is first isolated from the two tissues and the detection of mRNA encoded by a gene corresponding to a differentially expressed polynucleotide of the invention can be detected by, for example, in situ hybridization in tissue sections, reverse trascriptase-PCR, using Northern blots containing poly A+ mRNA, or any other direct or inderect RNA detection method. An increased or decreased expression of a given RNA in a diseased tissue compared to a normal tissue suggests that the transcript and/or the expressed protein has a role in the disease. Thus detection of a higher or lower level of mRNA corresponding to SEQ ID NO 1 or 3 relative to normal level is indicative of the presence of cancer in the patient.

mRNA expression levels in a sample can be determined by generation of a library of expressed sequence tags (ESTs) from the sample. The relative representation of ESTs in the library can be used to assess the relative representation of the gene transcript in the starting sample. The EST analysis of the test can then be compared to the EST analysis of a reference sample to determine the relative expression levels of the polynucleotide of interest.

Other mRNA analyses can be carried out using serial analysis of gene expression (SAGE) methodology (Velculescu et. Al. Science (1995) 270:484), differential display methodology (For example, U.S. Pat. No. 5,776,683) or hybridization analysis which relies on the specificity of nucleotide interactions.

Alternatively, the comparison could be made at the protein level. The protein sizes in the two tissues may be compared using antibodies to detect polypeptides in Western blots of protein extracts from the two tissues. Expression levels and subcellular localization may also be detected immunologically using antibodies to the corresponding protein. Further assay techniques that can be used to determine levels of a protein, such as a polypeptide of the present invention, in a sample derived from a host are well-known to those of skill in the art. A raised or decreased level of polypeptide expression in the diseased tissue compared with the same protein expression level in the normal tissue indicates that the expressed protein may be involved in the disease.

In the assays of the present invention, the diagnosis can be determined by detection of gene product expression levels encoded by at least one sequence set forth in SEQ ID NOS: 1 or 3.

A comparison of the mRNA or protein levels in a diseased versus normal tissue may also be used to follow the progression or remission of a disease.

A large number of polynucleotide sequences in a sample can be assayed using polynucleotide arrays. These can be used to examine differential expression of genes and to determine gene function. For example, arrays of the polynucleotide sequences SEQ ID NO: 1 or 3 can be used to determine if any of the polynucleotides are differentially expressed between a normal and cancer cell. In one embodiment of the invention, an array of oligonucleotides probes comprising the SEQ ID NO:1 or 3 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610-613 (1996)).

"Diagnosis" as used herein includes determination of a subject's susceptibility to a disease, determination as to whether a subject presently has the disease, and also the prognosis of a subject affected by the disease.

The present invention, further relates to a diagnostic kit for performing a diagnostic assay which comprises:
(a) a polynucleotide of the present invention, preferably the nucleotide sequence of SEQ ID NO: 1 or 3, or a fragment thereof;
(b) a nucleotide sequence complementary to that of (a);
(c) a polypeptide of the present invention, preferably the polypeptide of SEQ ID NO: 2, or a fragment thereof; or
(d) an antibody to a polypeptide of the present invention, preferably to the polypeptide of SEQ ID NO:2.

The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

In a further aspect the invention provides an antibody immunospecific for a polypeptide according to the invention or an immunological fragment thereof as hereinbefore defined. Preferably the antibody is a monoclonal antibody Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495-497), the trioma technique, the human B-cell hybridoma technique (Kozbor et al., Immunology Today (1983) 4:72) and the EBV-hybridoma technique (Cole et al., Monoclonal Antibodies and Cancer Therapy, 77-96, Alan R Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

The antibody of the invention may also be employed to prevent or treat cancer, particularly ovarian and colon cancer, autoimmune disease and related conditions.

Another aspect of the invention relates to a method for inducing or modulating an immunological response in a mammal which comprises inoculating the mammal with a polypeptide of the present invention, adequate to produce antibody and/or T cell immune response to protect or ameliorate the symptoms or progression of the disease. Yet another aspect of the invention relates to a method of inducing or modulating immunological response in a mammal which comprises, delivering a polypeptide of the present invention via a vector directing expression of the polynucleotide and coding for the polypeptide in vivo in order to induce such an immunological response to produce antibody to protect said animal from diseases.

It will be appreciated that the present invention therefore provides a method of treating abnormal conditions such as, for instance, cancer and autoimmune diseases, in particular, ovarian and colon cancer, related to either a presence of, an excess of, or an under-expression of, CASB618 polypeptide activity.

The present invention further provides for a method of screening compounds to identify those which stimulate or which inhibit the function of the CASB618 polypeptide. In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2): Chapter 5 (1991)). Screening methods will be known to those skilled in the art. Further screening methods may be found in for example D. Bennett et al., J Mol Recognition, 8:52-58 (1995); and K. Johanson et al., J Biol Chem, 270(16):9459-9471 (1995) and references therein.

Thus the invention provides a method for screening to identify compounds which stimulate or which inhibit the function of the polypeptide of the invention which comprises a method selected from the group consisting of:
(a) measuring the binding of a candidate compound to the polypeptide (or to the cells or membranes bearing the polypeptide) or a fusion protein thereof by means of a label directly or indirectly associated with the candidate compound;
(b) measuring the binding of a candidate compound to the polypeptide (or to the cells or membranes bearing the polypeptide) or a fusion protein thereof in the presense of a labeled competitior;
(c) testing whether the candidate compound results in a signal generated by activation or inhibition of the polypeptide, using detection systems appropriate to the cells or cell membranes bearing the polypeptide;
(d) mixing a candidate compound with a solution containing a polypeptide of claim 1, to form a mixture, measuring activity of the polypeptide in the mixture, and comparing the activity of the mixture to a standard; or
(e) detecting the effect of a candidate compound on the production of mRNA encoding said polypeptide and said polypeptide in cells, using for instance, an ELISA assay.

The polypeptide of the invention may be used to identify membrane bound or soluble receptors, if any, through standard receptor binding techniques known in the art. Well known screening methods may also be used to identify agonists and antagonists of the polypeptide of the invention which compete with the binding of the polypeptide of the invention to its receptors, if any.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:
(a) a polypeptide of the present invention;
(b) a recombinant cell expressing a polypeptide of the present invention;
(c) a cell membrane expressing a polypeptide of the present invention; or
(d) antibody to a polypeptide of the present invention; which polypeptide is preferably that of SEQ ID NO:2.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

Gene therapy may also be employed to effect the endogenous production of CASB618 polypeptide by the relevant cells in the subject. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Vaccine preparation is generally described in Pharmaceutical Biotechnology, Vol. 61 Vaccine Design—the subunit and adjuvant approach, edited by Powell and Newman, Plenurn Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1-1000 µg of protein, preferably 2-100 µg, most preferably 4-40 µg. An optimal amount for a particular vaccine can be ascertained by standard studies involving observation of antibody titres and other responses in subjects. Following an initial vaccination, subjects may receive a boost in about 4 weeks.

"Isolated" means altered "by the hand of man" from the natural state. If an "isolated" composition or substance occurs in nature, it has been changed or removes from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA including single and double stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987;

and Sequence Analysis Primer, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

The preferred algorithm used is FASTA. The preferred parameters for polypeptide or polynuleotide sequence comparison using this algorithm include the following:
Gap Penalty: 12
Gap extension penalty: 4
Word size: 2, max 6

Preferred parameters for polypeptide sequence comparison with other methods include the following:
1) Algorithm: Needleman and Wunsch, J. Mol. Biol. 48: 443-453 (1970)
Comparison matrix: BLOSSUM62 from Hentikoff and Hentikoff, Proc. Natl. Acad. Sci. USA. 89:10915-10919 (1992)
Gap Penalty: 12
Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:
1) Algorithm: Needleman and Wunsch, J. Mol. Biol. 48: 443453 (1970)
Comparison matrix: matches=+10, mismatch=0
Gap Penalty: 50
Gap Length Penalty: 3

A program useful with these parameters is publicly available as the "gap" program from Genetics Computer Group, Madison Wis. The aforementioned parameters are the default parameters for polynucleotide comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity (divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quntified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species and "paralog" meaning a functionally similar sequence when considered within the same species.

FIGURE LEGENDS

FIG. 1

FIG. 1 shows expression levels of CASB618 in matched colon normal and tumoral samples. The values are given in equivalent actin level.

N refers to normal colon, T refers to colon tumor.

FIG. 2

FIGS. 2A, 2B, 2C and 2D show the real-time PCR data of CASB618 expression in normal tissues.

The abbreviations stand for:

FIG. 2A: Co: colon; Ce: cervix; Bra: brain; Bo_Ma: bone marrow; Bl: bladder; Ao: aorta; Ad_Gl: adrenal gland FIG. 2B: Ov: ovary; Oe: Oesophage; Ly_No: lymph node; Lu: lung; Li: liver; Ki: kidney; Il: Ileum; He: heart; Fa_Tu: fallopian tube FIG. 2C: Sp: spleen; Sm_In: small intestine; Sk_Mu: skeletal muscle; Sk: skin; Re: rectum; Pr: prostate; Pl: placenta; Pa_Thy: parathyroid gland FIG. 2D: Tr: trachea; Thy: thyroid; Te: testis; St: stomach; Spl: spleen

FIG. 3

FIG. 3 shows a SDS-PAGE gel (12.5%) of the *E. coli* AR120/pRIT15081 extract, with or without induction with nalidixic acid; revealed with monoclonal antibody anti-NS1. Lane 1 is the Molecular weight marker; lane 2 shows the *E. coli* AR120/pRIT15081 3 hrs no induction; lane 3 shows the *E. coli* AR120/pRIT15081 3 hrs induced; lane 4 shows the *E. coli* AR120/pRIT15081 4h30 no induction; lane 5 shows the *E. coli* AR120/pRIT15081 4h30 induced.

FIG. 4

FIG. 4 shows SDS-PAGE gels of purified CASB618.

Lanes 1 and 8 show the Molecular weight marker; lane 2 shows the lysed cell pellet; lane 3 shows the 3 purified protein before dialyse; lane 4 shows the purified dialysed protein; lane 6 shows the purified dialysed protein 0.22 µm.

EXAMPLES

Example 1

Real-time RT-PCR Analysis

Real-time RT-PCR (U. Gibson. 1996. Genome Research: 6,996) is used to compare mRNA transcript abundance of the candidate antigen in matched tumour and normal colon tissues from multiple patients. In addition, mRNA levels of the candidate gene in a panel of normal tissues are evaluated by this approach.

Total RNA from normal and tumour colon is extracted from snap frozen biopsies using TriPure reagent (Boehringer). Total RNA from normal tissues is purchased from InVitrogen or is extracted from snap frozen biopsies using TriPure reagent. Poly-A$^+$ mRNA is purified from total RNA after DNAase treatment using oligo-dT magnetic beads (Dynal). Quantification of the mRNA is performed by spectrofluorimetry (VersaFluor, BioRad) using SybrII dye (Molecular Probes). Primers for real-time PCR amplification are designed with the Perkin-Elmer Primer Express software using default options for TaqMan amplification conditions.

Real-time reactions are assembled according to standard PCR protocols using 2 ng of purified mRNA for each reaction. SybrI dye (Molecular Probes) is added at a final dilution of 1/75000 for real-time detection. Amplification (40 cycles) and real-time detection is performed in a Perkin-Elmer Biosystems PE7700 system using conventional instrument settings. Ct values are calculated using the PE7700 Sequence Detector software. Two Ct values are obtained for each patient sample: the tumour Ct (CtT) and the matched normal colon Ct (CtN). Ct values obtained by real-time PCR are log-linearly related to the copy number of the target template. As the efficiency of PCR amplification under the prevailing experimental conditions is close to the theoretical amplification efficiency, $2^{(CtN-CtT)}$ is an estimate of the relative transcript levels in the two tissues (i.e. fold mRNA over-expression in tumor). Real-time PCR reactions are performed on biopsies from 23 patients. Some patient samples were measured twice. The level of mRNA over-expression is calculated as described for each patient, average level of mRNA over-expression for the candidate antigen and the proportion of patients over-expressing the candidate antigen is then calculated from this data set. The individual values are standardised with respect to actin in the same sample (ratio) and are shown in FIG. 1. A value of 1 thus corresponds to the same level of actin expression. The results are shown in a logarithmic scale.

A total of 81 normal tissue samples, representing 28 different tissues, were also tested by the same procedure. Ct values for the candidate antigen were compared to those of actin obtained with the same tissue sample. Standardised values are shown in FIGS. 2A-D.

Real-time PCR Results in Colon Cancer/Normal Colon Sample

Summary

| Patients over-expressing CASB618 in colon tumours (%) | Average level of over-expression in colon tumours (fold) |
|---|---|
| 18/23 (78%) | 125 |

Conclusion: CASB618 is overexpressed in a high proportion of tumors with respect to the normal adjacent colon. It is only marginally expressed by other normal tissues, in particular one prostate sample.

Example 2

DNA Microarrays

DNA micro-arrays are used to examine mRNA expression profiles of large collections of genes in multiple samples. This information is used to complement the data obtained by real-time PCR and provides an independent measure of gene expression levels in tumors and normal tissues.

Examples of current technologies for production of DNA micro-arrays include 1) The Affymetrix "GeneChip" arrays in which oligonucleotides are synthetized on the surface of the chip by solid phase chemical synthesis using a photolithographic process 2) DNA spotting technology in which small volumes of a DNA solution are robotically deposited and then immobilized onto the surface of a solid phase (e.g. glass). In both instances, the chips are hybridized with cDNA or cRNA which has been extracted from the tissue of interest (e.g. normal tissue, tumour etc. . . . ) and labeled with radioactivity or with a fluorescent reporter molecule. The labeled material is hybridized to the chip and the amount of probe bound to each sequence on the chip is determined using a specialized scanner. The experiment can be set-up with a single fluorescent reporter (or radioactivity) or, alternatively, can be performed using two fluorescent reporters. In this latter case, each of the two samples is labeled with one of the reporter molecules. The two labeled samples are then hybridized competitively to the sequences on the DNA chip. The ratio of the two fluorescent signals is determined for each sequence on the chip. This ratio is used to calculate the relative abundance of the transcript in the two samples. Detailed protocols are available from a number of sources including "DNA Microarrays: A practical approach. Schena M. Oxford University Press 1999" and the World Wide Web (search "cmgm.stanford.edu/pbrown/protocols/index"), (search "arrayit.com/DNA-Microarray-Protocols/") and specialized distributors (e.g. Affymetrix).

Example 3

EST Profiles

A complementary approach to experimental antigen tissue expression characterization is to explore the human "Expressed Sequence Tags" (ESTs) database. ESTs are small fragments of cDNA made from a collection of mRNA extracted from a particular tissue or cell line. Such databases currently provide a massive amount of ESTs ($10^6$) from several hundreds of cDNA tissue libraries, including tumoral tissues from various types and states of disease. By means of informatics tools (Blast), a comparison search of the CASB616 sequence is performed in order to have further insight into tissue expression.

EST Distribution of CASB618

| DbEST accession | ATG lib ID | Description | Category |
|---|---|---|---|
| NCBI: 1113567 | 882 | NCI_CGAP_Co3 | TC |
| NCBI: 1224225 | 937 | NCI_CGAP_Co2 | TC |
| NCBI: 1271870 | 988 | NCI_CGAP_Co12 | TC |
| NCBI: 1316079 | 889 | NCI_CGAP_Thy1 | TA |
| NCBI: 2035497 | 1079 | NCI_CGAP_Co8 | TC |
| NCBI: 2048268 | 1079 | NCI_CGAP_Co8 | TC |
| NCBI: 2054603 | 1079 | NCI_CGAP_Co8 | TC |
| NCBI: 2081390 | 1079 | NCI_CGAP_Co8 | TC |
| NCBI: 2129969 | 1079 | NCI_CGAP_Co8 | TC |
| NCBI: 2489139 | 1728 | Soares_Dieckgraefe_ | Dc |
| NCBI: 2489206 | 1728 | Soares_Dieckgraefe_ | Dc |
| NCBI: 2600163 | 882 | NCI_CGAP_Co3 | TC |
| NCBI: 2641414 | 882 | NCI_CGAP_Co3 | TC |
| NCBI: 2831741 | 937 | NCI_CGAP_Co2 | TC |
| NCBI: 2914582 | 910 | NCI_CGAP_Pr22 | NP |
| NCBI: 3111692 | 1728 | Soares_Dieckgraefe_ | Dc |
| NCBI: 3112040 | 1728 | Soares_Dieckgraefe_ | Dc |
| NCBI: 3043263 | 1460 | NCI_CGAP_Pan1 | Tep |
| NCBI: 3119272 | 1728 | Soares_Dieckgraefe_ | Dc |
| NCBI: 3138950 | 882 | NCI_CGAP_Co3 | TC |
| NCBI: 3181303 | 1728 | Soares_Dieckgraefe_ | Dc |
| NCBI: 2908798 | 882 | NCI_CGAP_Co3 | TC |
| NCBI: 2909226 | 937 | NCI_CGAP_Co2 | TC |

TC: colon tumor;
Dc: diseased colon;
NP; normal prostate;
Tep: epithelial tumor;
Ta: other tumor type.

The high proportion of colon cancer ESTs thus clearly suggests an overexpression of this gene in colon cancer. Additionally, other tumors (pancreas, thyroid) could also express the gene.

Example 4

Northern-Southern Blot Analysis

Limited amounts of mixed tumour and matched normal colon cDNA are amplified by Advantage PCR (see above). Messenger RNA from multiple normal tissues is also amplified using the same procedure. The amplified cDNA (1 µg) is electrophoresed on a 1.2% agarose gel and transferred onto a nylon membrane. The membrane is hybridised (ALkPhos Direct System) with a probe prepared using a fragment of the candidate TAA cDNA. Northern-Southern analysis provides information on transcript size, presence of splice variants and transcript abundance in tumour and normal tissues.

Example 5

Northern Blot Analysis

Northern blots are produced according to standard protocols using 1 µg of poly A+ mRNA. Radioactive probes are prepared using the Ready-to-Go system (Pharmacia).

Example 6

Identification of the Full Length cDNA Sequence

Colon tumour cDNA libraries are constructed using the Lambda Zap II system (Stratagene) from 5 µg of polyA+ mRNA. The supplied protocol is followed except that SuperscriptII (Life Technologies) is used for the reverse transcription step. Oligo dT-primed and random-primed libraries are constructed. About 1.5×106 independent phages are plated for each screening of the library. Phage plaques are transferred onto nylon filters and hybridised using a cDNA probe labelled with AlkPhos Direct. Positive phages are detected by chemiluminescence. Positive phage are excised from the agar plat, eluted in 500 µSM buffer and confirmed by gene-specific PCR. Eluted phages are converted to single strand M13 bacteriophage by in vivo excision. The bacteriophage is then converted to double strand plasmid DNA by infection of E. coli. Infected bacteria are plated and submitted to a second round of screening with the cDNA probe. Plasmid DNA is purified from positive bacterial clones and sequenced on both strands.

When the full length gene cannot be obtained directly from the cDNA library, missing sequence is isolated using RACE technology (Marathon Kit, ClonTech.). This approach relies on reverse transcribing mRNA into double strand cDNA, ligating linkers onto the ends of the cDNA and amplifying the desired extremity of the cDNA using a gene-specific primer and one of the linker oligonucleotides. Marathon PCR products are cloned into a plasmid (pCRII-TOPO, InVitrogen) and sequenced.

The obtained sequence (SEQ ID NO:1) has a putative open reading frame of 259 amino acids (SEQ ID NO:2). The deduced protein sequence was submitted to prediction algorithms for cellular localisation (PSORT: search "psort.nibb.ac.jp" and TopPred: search "www.biokemi.su.se/.about-.server/toppred2/toppred_source"). It is predicted to have 4 to 5 transmembrane segments; only one of the 2 methods used predicts the signal sequence. There is a potential leucine zipper motif overlapping one of the predicted transmembrane segments. There are 3 potential N-glycosylation sites. Subcellular localisation is unclear, plasma membrane being the most probable.

Example 7

7.1 Expression and Purification of Tumour-specific Antigens

Expression in microbial hosts, or alternatively in vitro transcription/translation, is used to produce the antigen of the invention for vaccine purposes and to produce protein fragments or whole protein for rapid purification and generation of antibodies needed for characterization of the naturally expressed protein by immunohistochemistry or for follow-up of purification.

Recombinant proteins may be expressed in two microbial hosts, E. coli and in yeast (such as Saccharomyces cerevisiae or Pichia pastoris), Pichia. This allows the selection of the expression system with the best features for this particular antigen production. In general, the recombinant antigen will be expressed in E. coli and the reagent protein expressed in yeast.

The expression strategy first involves the design of the primary structure of the recombinant antigen. In general an expression fusion partner (EFP) is placed at the N terminal extremity to improve levels of expression that could also include a region useful for modulating the immunogenic properties of the antigen, an immune fusion partner (IFP). In addition, an affinity fusion partner (AFP) useful for facilitating further purification is included at the C-terminal end.

When the recombinant strains are available, the recombinant product is characterized by the evaluation of the level of expression and the prediction of further solubility of the protein by analysis of the behavior in the crude extract.

After growth on appropriate culture medium and induction of the recombinant protein expression, total extracts are analyzed by SDS-PAGE. The recombinant proteins are visualized in stained gels and identified by Western blot analysis using specific antibodies.

A comparative evaluation of the different versions of the expressed antigen will allow the selection of the most promising candidate that is to be used for further purification and immunological evaluation.

Expression in *E. coli* AR120

The following construct was designed and made: the gene CASB618 carrying deletions of the N-terminus and C-terminus (Δ 1-74; Δ 247-320 aa) was cloned in vector pMG81 (pr PL long), with the addition of an IFP (NS1 DNA sequence encoding the N-terminal 1 to 81 amino acids of the NS1 protein of Influenza virus) at the N-terminus, and a C-terminal histidine tail (SEQ ID NO:4)

NS1- Met Thr Met | C 61-8 | Thr Ser Gly 6xHIS
75        246

The obtained plasmid is called pRIT 15081. The acid nalidixic inducible host cell *E. coli* AR120 is used. Induction of three litres of *E. coli* cultures in LB medium+Kannamycin was obtained by adding acid nalidixic to a final concentration of 60 ng/ml. The cultures were incubated 4h30 at 37° C.

The pellet obtained after centrifugation of the induced cultures was resuspended in 60 ml of PBS buffer. The cells were subsequently lysed using a French press. The lysate was then centrifugation for 20 minutes at 16000 g. We found the expressed protein in the pellet (FIG. 3).

The purification scheme follows a classical approach based on the presence of an His affinity tail in the recombinant protein. In a typical experiment the disrupted cells are filtered and the acellular extracts loaded onto an Ion Metal Affinity Chromatography (IMAC; Ni++NTA from Qiagen) that will specifically retain the recombinant protein. The retained proteins are eluted by 0-500 mM Imidazole gradient (possibly in presence of a detergent) in a phosphate buffer.

The purification scheme is detailed below.

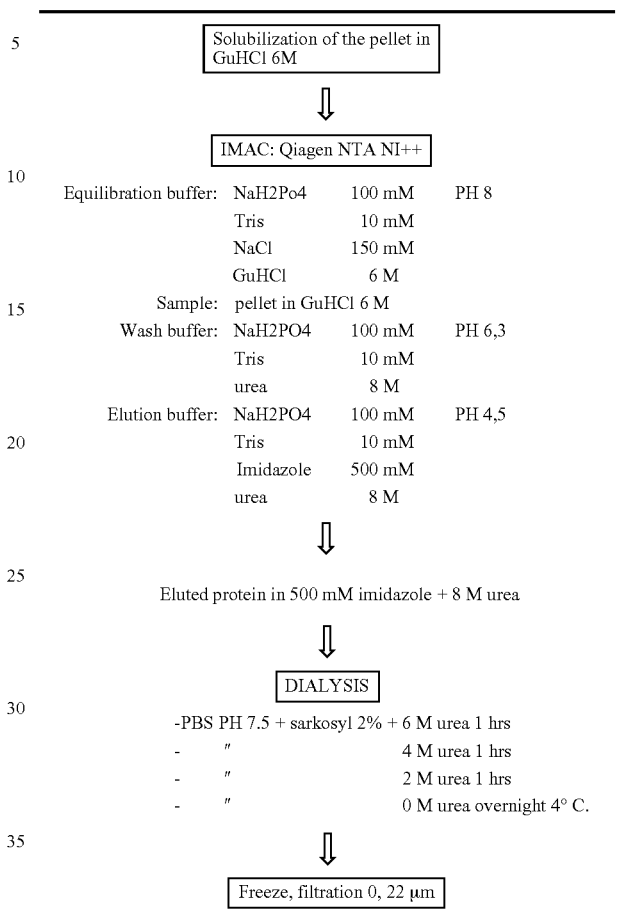

An estimation of the final concentration (1 mg/ml) is obtained by a Lowry protein assay on the final purified product (see FIG. 4).

In Vitro Transcription/Translation

The CASB618 gene product was characterised by coupled transcription/translation in vitro. Full-length coding sequence of clone CASB618 was cloned into SP72 vector (Promega), a vector allowing in vitro transcription. In vitro expression using TNT T7 coupled reticulocyte lysate (Promega cat. No. L4611) with incorporation of S35 methionine shows a product of 35 Kd, which is reduced to 30 Kd in presence of canine pancreatic microsomal membranes (Promega cat. No. Y4041). This result suggests processing of the signal peptide in accordance with the signal peptide prediction of 47 amino acids (, and suggests that the protein in vivo is membrane anchored or secreted. For these experiments, protocols recommended by Promega were followed.

7.2 Antibody Production and Immunohistochemistry

Small amounts of relatively purified protein can be used to generate immunological tools in order to a) detect the expression by immunohistochemistry in normal or cancer tissue sections;

b) detect the expression, and to follow the protein during the purification process (ELISA/Western Blot); or c) characterise/quantify the purified protein (ELISA).

7.2.1 Polyclonal Antibodies:

Immunization 2-3 Rabbits are immunised, intramuscularly (I.M.), 3 times at 3 weeks intervals with 100 μg of protein, formulated in the adjuvant 3D-MPL/QS21. Three weeks after each immunisation a blood sample is taken and the antibody titer estimated in the serum by ELISA using the protein as coating antigen following a standard protocol.

ELISA 96 well microplates (maxisorb Nunc) are coated with 5 μg of protein overnight at 4° C. After 1 hour saturation at 37° C. with PBS NCS 1%, serial dilution of the rabbit sera is added for 1H 30 at 37° C. (starting at 1/10). After 3 washings in PBS Tween, anti rabbit biotinylated anti serum (Amersham) is added (1/5000). Plates are washed and peroxydase coupled streptavidin (1/5000) is added for 30 min at 37° C. After washing, 50 μl TMB (BioRad) is added for 7 min and the reaction then stopped with $H_2SO_4$ 0.2M. The OD can be measured at 450 nm and midpoint dilutions calculated by SoftmaxPro.

7.2.2 Monoclonal Antibodies:

Immunization

5 BALB/c mice are immunized 3 times at 3 week intervals with 5 μg of purified protein. Bleedings are performed 14 days post II and 1 week post 3. The sera are tested by Elisa on purified protein used as coated antigen. Based on these results (midpoint dilution>10000) one mouse is selected for fusion Fusion/HAT Selection Spleen cells are fused with the SP2/0 myeloma according to a standard protocol using PEG 40% and DMSO 5%. Cells are then seeded in 96 well plates $2.5 \times 10^4$-$10^5$ cells/well and resistant clones will be selected in HAT medium. The supernatant of these hybridomas will be tested for their content in specific antibodies and when positive, will be submitted to 2 cycles of limited dilution. After 2 rounds of screening, 3 hybridomas will be chosen for ascitis production.

7.2.3 Immunohistochemistry

When antibodies are available, immuno staining is performed on normal or cancer tissue sections, in order to determine:
- the level of expression of the antigen of the invention in cancer relative to normal tissue or
- the proportion of cancer of a certain type expressing the antigen
- if other cancer types also express the antigen
- the proportion of cells expressing the antigen in a cancer tissue Tissue Sample Preparation After dissection, the tissue sample is mounted on a cork disk in OCT compound and rapidly frozen in isopentane previously super cooled in liquid nitrogen (−160° C.). The block will then be conserved at −70° C. until use. 7-10 μm sections will be realised in a cryostat chamber (−20, −30° C.).

Staining

Tissue sections are dried for 5 min at room Temperature (RT), fixed in acetone for 10 min at RT, dried again, and saturated with PBS 0.5% BSA 5% serum. After 30 min at RT either a direct or indirect staining is performed using antigen specific antibodies. A direct staining leads to a better specificity but a less intense staining whilst an indirect staining leads to a more intense but less specific staining.

7.3 Analysis of Human Cellular Immune Responses to the Antigen of the Invention The immunological relevance of the antigen of the invention can be assessed by in vitro priming of human T cells. All T cell lymphocyte lines and dendritic cells are derived from PBMCs (peripheral blood mononuclear cells) of healthy donors (preferred HLA-A2 subtype). An HLA-A2.1/$K^b$ transgenic mice is also used for screening of HLA-A2.1 peptides.

Newly discovered antigen-specific CD8+ T cell lines are raised and maintained by weekly in vitro stimulation. The lytic activity and the γ-IFN production of the CD8 lines in response to the antigen or antigen derived-peptides is tested using standard procedures.

Two strategies to raise the CD8+ T cell lines are used: a peptide-based approach and a whole gene-based approach. Both approaches require the full-length cDNA of the newly discovered antigen in the correct reading frame to be either cloned in an appropriate delivery system or to be used to predict the sequence of HLA binding peptides.

Peptide-based Approach

The HLA-A2 binding peptide sequences are predicted either by the Parker's algorithm (Parker, K. C., M. A. Bednarek, and J. F. Coligan. 1994. Scheme for ranking potential HLA-A2 binding peptides based on independent binding of individual peptide side-chains. J. Immunol. 152:163 and search "bimas.dcrt.nih.gov/molbio/hla_bind") or the Rammensee method (Rammensee, Friede, Stevanovic, MHC ligands and peptide motifs: 1st listing, Immunogenetics 41, 178-228, 1995; Rammensee, Bachmann, Stevanovic: MHC ligands and peptide motifs. Landes Bioscience 1997, and search "134.2.96.221/scripts/hlaserver.dll/home"). Peptides are then screened in the HLA-A2.1/K.sup.b transgenic mice model (Vitiello et al.). The sequence used to perform the prediction is EPHB2v, as it is identical to EPHB2 with an additional C-terminal sequence extension.

a) Predicted Epitopes Binding the HLA_A0201 Allele:

a.1) HLA-A*0201 Nonamers

| Position | 1 | 2 | 3 | 4 | 5 | 6 | 7 | 8 | 9 | Rammensee score | Parker score° | SEQ ID NO |
|---|---|---|---|---|---|---|---|---|---|---|---|---|
| 262 | F | L | G | G | A | V | V | S | L | 31 | 226.014 | 5 |
| 24 | L | L | I | V | I | L | V | F | L | 30 | 459.398 | 6 |
| 253 | T | L | A | T | G | V | L | C | L | 29 |  | 7 |
| 203 | P | L | Y | G | G | L | A | L | L | 28 |  | 8 |
| 149 | G | L | P | D | P | V | L | Y | L | 28 | 1107.961 | 9 |
| 100 | G | L | L | V | G | L | E | G | I | 28 |  | 10 |
| 53 | W | L | V | R | V | L | L | S | L | 27 | 226.014 | 11 |
| 62 | F | I | G | A | E | L | V | A | V | 26 | 101.181 | 12 |
| 260 | C | L | F | L | G | G | A | V | V | 25 | 105.510 | 13 |
| 196 | V | L | L | S | T | P | A | P | L | 25 | 134.369 | 14 |
| 60 | S | L | F | I | G | A | E | I | V | 25 |  | 15 |
| 210 | L | L | T | T | G | A | F | A | L | 24 | 210.633 | 16 |
| 104 | G | L | E | G | I | N | I | T | L | 24 |  | 17 |

-continued

| Position | 1 | 2 | 3 | 4 | 5 | 6 | 7 | 8 | 9 | Rammensee score | Parker score° | SEQ ID NO |
|---|---|---|---|---|---|---|---|---|---|---|---|---|
| 34 | L | A | A | S | F | L | L | I | L | 24 | | 18 |
| 222 | F | A | L | A | S | I | S | S | V | 23 | | 19 |
| 216 | F | A | L | F | G | V | F | A | L | 23 | | 20 |
| 192 | L | L | S | N | V | L | L | S | T | 23 | | 21 |
| 138 | Y | A | A | E | Y | A | N | A | L | 23 | | 22 |
| 33 | A | L | A | A | S | F | L | L | I | 23 | | 23 |
| 31 | F | L | A | L | A | A | S | F | L | 23 | 540.469 | 24 |
| 21 | S | V | P | L | L | I | V | I | L | 23 | | 25 |
| 174 | H | L | A | G | H | Y | A | S | A | 22 | | 26 |
| 112 | L | T | G | T | P | V | H | Q | L | 22 | | 27 |
| 97 | A | R | V | G | L | L | V | G | L | 22 | | 28 |
| 91 | S | A | A | R | V | T | A | R | V | 22 | | 29 |
| 73 | S | A | E | W | F | V | G | T | V | 22 | | 30 |
| 27 | V | I | L | V | F | L | A | L | A | 22 | | 31 |
| 308 | A | A | L | P | D | L | K | C | I | 21 | | 32 |
| 299 | I | L | G | D | P | L | H | K | Q | 21 | | 33 |
| 258 | V | L | C | L | F | L | G | G | A | 21 | | 34 |
| 217 | A | L | F | G | V | F | A | L | A | 21 | | 35 |
| 207 | G | L | A | L | L | T | T | G | A | 21 | | 36 |
| 40 | L | I | L | P | G | I | R | G | H | 21 | | 37 |
| 16 | H | A | A | G | F | S | V | P | L | 21 | | 38 |
| 312 | D | L | K | C | L | T | T | N | L | 20 | | 39 |
| 234 | P | L | R | L | G | S | S | A | L | 20 | | 40 |
| 209 | A | L | L | T | T | G | A | F | A | 20 | 101.099 | 41 |
| 26 | L | V | I | L | V | F | L | A | L | 20 | | 42 |
| 17 | A | A | G | F | S | V | P | L | L | 20 | | 43 |
| 154 | V | L | Y | L | A | E | K | F | T | | 222.964 | 44 |
| 244 | T | Q | Y | G | A | A | F | W | W | | 719.848 | 45 |
| 185 | W | V | A | F | C | F | W | L | L | | 122.527 | 46 |

°Estimate of half time of disassociation of a molecule containing this subsequence a.2) HLA A02_01 Decamers

| Position | sequence | Rammensee score* | Parker score° | SEQ ID NO |
|---|---|---|---|---|
| 33 | ALAASFLLLL | 29 | | 47 |
| 223 | ALASISSVPL | 26 | | 48 |
| 111 | TLTGTPVHQL | 26 | | 49 |
| 209 | ALLTTGAFAL | 25 | 458.437 | 50 |
| 23 | PLLIVILVFL | 25 | | 51 |
| 272 | YVRPSALRTL | 24 | | 52 |
| 261 | LFLGGAVVSL | 24 | | 53 |
| 226 | SISSVPLCPL | 24 | | 54 |
| 58 | LLSLFIGAEI | 24 | | 55 |
| 191 | WLLSNVLLST | 23 | 291.716 | 56 |
| 61 | LFLGAEIVAV | 23 | | 57 |
| 31 | FLALAASFLL | 23 | 569.949 | 58 |
| 16 | HAAGFSVPLL | 23 | | 59 |
| 269 | SLQYVRPSAL | 22 | | 60 |
| 258 | VLCLFLGGAV | 22 | | 61 |
| 252 | VTLATGVLCL | 22 | | 62 |
| 101 | LLVGLEG1NI | 22 | | 63 |
| 25 | LIVILVFLAL | 22 | | 64 |
| 24 | LLIVILVFLA | 22 | 112.664 | 65 |
| 298 | LILGDPLHKQ | 21 | | 66 |
| 183 | TLWVAFCFWL | 21 | 21493.266 | 67 |
| 149 | GLPDPVLYLA | 21 | | 68 |
| 145 | ALEKGLPDPV | 21 | | 69 |
| 96 | TARVGLLVGL | 21 | | 70 |
| 72 | FSAEWFVGTV | 21 | | 71 |
| 175 | LAGHYASATL | 20 | | 72 |
| 148 | KGLPDPVLYL | 20 | | 73 |
| 104 | GLEGINITLT | 20 | | 74 |
| 52 | FWLVRVLLSL | 20 | | 75 |
| 21 | SVPLLIVILV | 20 | | 76 |
| 69 | AVHFSAEWFV | | 251.039 | 77 |

°Estimate of halftime of disassociation of a molecule containing this subsequence Briefly, transgenic mice are immunized with adjuvanted HLA-A2 peptides, those unable to induce a CD8 response (as defined by an efficient lysis of peptide-pulsed autologous spleen cells) will be further analyzed in the human system.

Human dendritic cells (cultured according to Romani et al.) will be pulsed with peptides and used to stimulate CD8-sorted T cells (by Facs). After several weekly stimulations, the CD8 lines will be first tested on peptide-pulsed autologous BLCL (EBV-B transformed cell lines). To verify the proper in vivo processing of the peptide, the CD8 lines will be tested on cDNA-transfected tumour cells (HLA-A2 transfected LnCaP, Skov3 or CAMA tumour cells).

Whole Gene-based Approach

CD8+ T cell lines will be primed and stimulated with either gene-gun transfected dendritic cells, retrovirally transduced B7.1-transfected fibroblasts, recombinant pox virus (Kim et al.) or adenovirus (Butterfield et al.) infected dendritic cells. Virus infected cells are very efficient to present antigenic peptides since the antigen is expressed at high level but can only be used once to avoid the over-growth of viral T cells lines.

After alternated stimulations, the CD8+ lines are tested on cDNA-transfected tumour cells as indicated above. Peptide specificity and identity is determined to confirm the immunological validation.

REFERENCES

Vitiello et al. (L. Sherman), J. Exp. Med., J. Exp. Med, 1991, 173:1007-1015.

Romani et al., J. Exp. Med., 1994, 180:83-93.

Kim et al., J. Immunother., 1997, 20:276-286.

Butterfield et al., J. Immunol., 1998, 161:5607-5613.

All publications, including but not limited to patents and patent applications, cited in this specification are herein incorporated by reference as if each individual publication were specifically and individually indicated to be incorporated by reference herein as though fully set forth.

of the cDNA and amplifying the desired extremity of the cDNA using a gene-specific primer and one of the linker oligonucleotides. Marathon PCR products are cloned into a plasmid and sequenced.

The invention claimed is:

1. An isolated polynucleotide comprising the polynucleotide of SEQ ID NO:3, or the full complement thereof.

2. A kit for screening a patient for the presence of colon cancer by measuring the expression of a polynucleotide marker, said kit comprising the polynucleotide of claim 1.

* * * * *